US006670383B2

(12) United States Patent
Xu et al.

(10) Patent No.: US 6,670,383 B2
(45) Date of Patent: Dec. 30, 2003

(54) PYRANOCOUMARIN COMPOUNDS AS A NOVEL PHARMACOPHORE WITH ANTI-TB ACTIVITY

(75) Inventors: Ze-Qi Xu, Woodridge, IL (US); Krzysztof Pupek, Downers Grove, IL (US); Livia Enache, Plainfield, IL (US); Michael T. Flavin, Darien, IL (US)

(73) Assignee: Advanced Life Sciences, Inc., Woodridge, IL (US)

(*) Notice: Subject to any disclaimer, the term of this patent is extended or adjusted under 35 U.S.C. 154(b) by 0 days.

(21) Appl. No.: 10/099,726

(22) Filed: Mar. 15, 2002

(65) Prior Publication Data

US 2003/0083369 A1 May 1, 2003

Related U.S. Application Data

(60) Provisional application No. 60/276,531, filed on Mar. 16, 2001.

(51) Int. Cl.[7] .............................................. A61K 31/35
(52) U.S. Cl. ..................... 514/355; 514/453; 514/454; 514/457; 549/277; 549/282; 549/289
(58) Field of Search ................................ 514/453, 454, 514/457, 455; 549/277, 282, 289

(56) References Cited

U.S. PATENT DOCUMENTS

| | | | | |
|---|---|---|---|---|
| 5,489,697 A | 2/1996 | Boulanger et al. | ........... | 549/278 |
| 5,840,921 A | 11/1998 | Flavin et al. | ............... | 549/282 |
| 5,847,164 A | 12/1998 | Flavin et al. | ............... | 549/278 |
| 5,859,050 A | 1/1999 | Flavin et al. | ............... | 514/453 |
| 5,869,324 A | 2/1999 | Flavin et al. | ............... | 435/280 |
| 5,872,264 A | 2/1999 | Flavin et al. | ............... | 549/277 |
| 5,874,591 A | 2/1999 | Flavin et al. | ............... | 549/282 |
| 5,892,060 A | 4/1999 | Flavin et al. | ............... | 549/277 |
| 5,977,385 A | 11/1999 | Flavin et al. | ............... | 549/282 |
| 5,981,770 A | 11/1999 | Flavin et al. | ............... | 549/282 |
| 6,043,271 A | 3/2000 | Flavin et al. | ............... | 514/453 |
| 6,277,879 B1 | 8/2001 | Xu et al. | .................... | 514/453 |

FOREIGN PATENT DOCUMENTS

| | | |
|---|---|---|
| AU | 704247 | 4/1996 |
| AU | 730178 | 2/1999 |
| EP | 1 054 007 | 11/2000 |
| WO | WO 96/04263 | 2/1996 |
| WO | WO 98/38193 | 9/1998 |

OTHER PUBLICATIONS

Lane, C., "Sodium Cyanoborohydride–A Highly Selective Reducing Agent for Organic Functional Groups," *Synthesis*, p. 135–146 (1975).

Raviglione, M., et al., "Global Epidemilogy of Tuberculosis," *JAMA*, vol. 273, p. 220–226 (1995).

Stokstad, E., "Drug–Resistant TB on the Rise," *Science*, vol. 287 p. 2391 (2000).

Suling, W., et al., "Susceptibilities of *Mycobacterium tuberculosis* and *Mycobacterium avium* complex to lipophilic deazapteridine derivatives, inhibitors of dihydrofolate reductase," *Journal of Antimicrobial Chemotherapy*, vol. 42, p. 811–815 (1998).

Zembower, D., et al., "Structural Analogues of the Calanolide Anti–HIV Agents. Modification of the *trans*–10, 11–Dimethyldihydropyran–12–ol Ring (Ring C)[1]," *J. Med. Chem*, vol. 40, p. 1005–1017 (1997).

Collins, et al., "Microplate Alamar Blue Assay versus BACTEC 460 System for High–Throughput Screening of Compounds against *Mycobacterium tuberculosis* and *Mycobacterium avium*," Antimicrobial Agents and Chemotherapy, vol. 41 [5], (1997), pp. 1004–1009, U.S.

Creagh, Ph.D., et al., "Preliminary Clinical Safety Profile (+)–Calanolide A—A New Novel NNRTI," 5th Conference on Retroviruses and Opportunistic Infections, Jan. 22–26, 1997, Abstract 477, U.S.

Frank, et al., "Safety Assessment of (+–Calanolide A, A Naturally Occurring Anti–HIV Agent," 4th Conference on Retroviruses and Opportunistic Infections, Jan. 22–26, 1997, Abstract No. 225, U.S.

Inderlied, et al., "Antimycobacterial Agents and Susceptibility Tests," Manual of Clinical Microbiology, 6th Ed., (1995), pp. 1601–1623, U.S.

Johnsson, et al., "Studies on the Mechanism of Action of Isoniazid and Ethionamide in the Chemotherapy of Tuberculosis," J. Am. Chem. Soc., vol. 117, (1995), pp. 5009–5010, U.S.

Ormerod, "Rifampicin and isoniazid prophylactic chemotherapy for tuberculosis," Arch. Dis. Child, vol. 78, (1998), pp. 169–171, U.S.

Rahman et al., "Anti–tuberculosis Activity of Quassinoids," Chem. Pharm. Bull., vol. 45 [9], (1997), pp. 1527–1529, U.S.

Winder, et al., "Inhibition by Isoniazid of Synthesis of Mycolic Acids in Mycobacterium tuberculosis," Journal of General Microbiology, vol. 63, (1970), pp. 41–48, Great Britain.

Barrow, E., et al., "Use of Microsphere Technology for Targeted Delivery of Rifampin to *Mycobacterium tuberculosis*—Infected Macrophages," *Antimicrobial. Agents Chemotherapy*, vol. 42, p. 2682–2689 (1998).

(List continued on next page.)

*Primary Examiner*—Amelia Owens
(74) *Attorney, Agent, or Firm*—McDonnell Boehnen Hulblert & Berghoff

(57) ABSTRACT

The present invention relates to compounds and compositions useful in treating or preventing conditions and diseases related to Mycobacterium infection, and methods of use directed thereto.

35 Claims, 3 Drawing Sheets

OTHER PUBLICATIONS

Deshapande, P., et al., "Synthesis of Optically Active Calanolides A and B," *J. Org. Chem.*; vol. 60, p. 2964–2965 (1995).

Fabiano, E., et al., "A Simple Conversion of Alcohols into Amines," Communications, Synthesis, p. 190–192 (1987).

Flavin, M., et al., "Synthesis Chromatographic Resolution, and Anti–Human Innunodeficiency Virus Activity of (±)–Calanolide A and its Enantiomers," *J. Med. Chem.*; vol. 39, p. 1303–1313 (1996).

Galinis, D., et al., "Structure–Activity Modifications of the HIV–1 Inhibitors (+)– Calanolide A and (–)–Calanolide B$^1$," *J. Med. Chem.*, vol. 39, p. 4507–4510 (1996).

Heifets, L., et al., "Development of Rifapentine Susceptibility Tests for *Mycobacterium tuberculosis*," Antimicrob. *Agents Chemother.*; vol. 43, p. 25–28 (1999).

Kling, J., *Modern Drug Discovery*, 1999; (Jan./Feb.): 32, 33, 36, 28, 40, 42, 45.

Kucherenko, A., et al., "Novel Approach for Synthesis of (±)–Calanolide A and Its Anti–HIV Activity," *Tetrahedron Letters*, vol. 36, p. 5475–5478 (1995).

Harries, A.D.; Mahler, D. TB/HIV A Clinical Manual Published by the World Health Organization 1996, Printer: Stabilimento Tipografico Ferrero s.r.l.–Romano Canavese [TO], Italy.

Zembower, D.E.; Chandraseker, P.; Liao, S.; Xu, Z.–Q.; Flavin, M.T. *213$^{th}$ National Meeting of the American Chemical Society, Division of Medicinal Chemistry*, San Francisco, Apr. 13–17, 1997, Abstract 111.

Lopez et al., "Disease Control Priorties in Developing Countries", Jamison, D.T., Mosely, W.H. Eds. (Oxford Univ. Press for the World Bank, New York, 1993), Chapter 2, p. 35–50.

Murray, C. et al., "Disease Control Priorties in Developing Countries", Jamison, D.T., Mosely, W.H. Eds. (Oxford Univ. Press for the World Bank, New York, 1993), Chapter 65 p. 233–259.

Figure 1: Structures of Pyranocoumarin Compounds
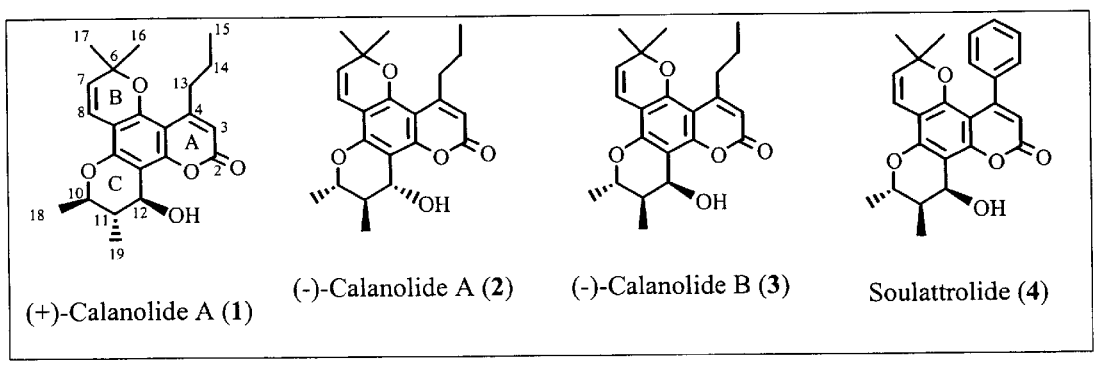
(+)-Calanolide A (1)　　(-)-Calanolide A (2)　　(-)-Calanolide B (3)　　Soulattrolide (4)
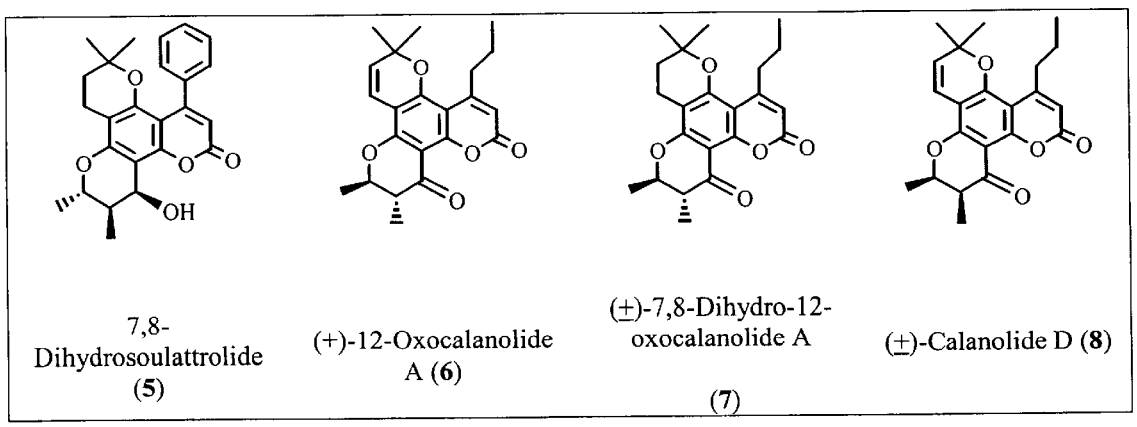
7,8-Dihydrosoulattrolide (5)　　(+)-12-Oxocalanolide A (6)　　(±)-7,8-Dihydro-12-oxocalanolide A (7)　　(±)-Calanolide D (8)

Figure 2: Structural Features in Pyranocoumarins Critical for Anti-TB Activity
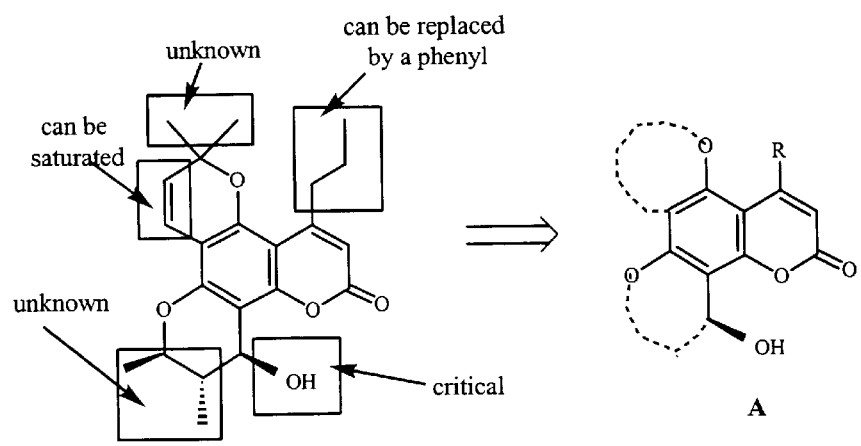
Selected General Structures Types I-IV
| Type I | Type II | Type III | Type IV |
|---|---|---|---|

Figure 3: Design, Synthesis and Evaluation of Pyranocoumarin Analogues
| Category | Compound Examples |
|---|---|
| Type I | 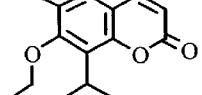 |
| Type II | 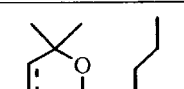 |
| Type III | 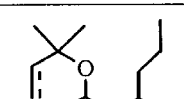  $R_1$ = H, Me, n-Pr, c-PrCH$_2$, Ph<br>$R_2$ = H, Me, Et, allyl, t-Bu, Ac<br>$R_3$ = H, Me, Et, allyl, t-Bu, O, OH<br>$R_4$ = H, Me, Et, allyl, t-Bu, OH<br>$R_5$ = H, Me, Et, allyl, t-Bu, Ac |
| Type IV | 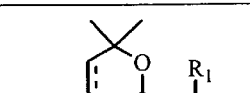 |

PYRANOCOUMARIN COMPOUNDS AS A NOVEL PHARMACOPHORE WITH ANTI-TB ACTIVITY

PRIORITY DATA AND GOVERNMENTAL RIGHTS

This application claims priority to U.S. Provisional application Ser. No. 60/276,531, filed Mar. 16, 2001. This work was supported in part by the National Institutes of Health (NIH) through SBIR Grant (#1 R43 AI49053-01). Accordingly, the United States government may have certain rights to the invention.

FIELD OF THE INVENTION

The present invention relates to methods for the treatment of conditions related to Mycobacterium tuberculosis infection. The invention also relates to compounds and compositions useful in the treatment of Mycobacterium tuberculosis infection. The invention further relates to a method useful in the stepwise reductive amination of ketones.

BACKGROUND OF THE INVENTION

Infectious diseases remain the largest cause of death in the world today, greater than cardiovascular disease or cancer[1]. Tuberculosis (TB), caused by Mycobacterium tuberculosis, a facultative intracellular bacillus, is the world's number one killer among the infectious diseases and the leading cause of death among women of reproductive age[2]. Even though the improved methods of prevention, detection, diagnosis, and treatment have greatly reduced the number of people who contract the disease and die from it, the emergence of multidrug-resistant (MDR) strains[3] and the global human immunodeficiency virus (HIV) pandemic have amplified the incidence of TB.

It has been estimated one-third (about 2 billion) of the world's population, including 15 million Americans, is infected with M. tuberculosis[4]. The lifetime risk of developing TB is approximately 10% of infected persons, while the remaining 90% have latent infection with viable bacilli. This 10% rate of TB accounts for the 8 million cases of each year, resulting in 3 million deaths. The gravity of the situation led the World Health Organization (WHO) in 1993 to declare TB a global emergency in an attempt to heighten public and political awareness.

HIV is the most powerful factor known to increase the risk of TB. At first, HIV increases a person's susceptibility to infection with M. tuberculosis. In 1995, about one third of the 17 million HIV-infected people worldwide were also co-infected with M. tuberculosis[5]. As HIV infection progresses, CD4+ lymphocytes decline in number and function and, therefore, the immune system is less able to prevent the growth and local spread of M. tuberculosis, rendering a rapid progression of TB infection to disease. An individual co-infected with HIV and M. tuberculosis has a 10 times greater risk of developing TB, compared to an individual who is not infected with HIV. On the other hand, TB infection in an HIV-infected person may allow HIV to multiply more quickly and lead to a more rapid disease progression of AIDS[5].

The recommended treatment of TB is Directly Observed Therapy Short-course (DOTS), which uses a combination of drugs with isoniazid and rifampin taken over 6 months, supplemented with pyrazinamide for the first 2 months, and addition of ethambutol when isoniazid resistance is suspected. DOTS is generally successful, even though the treatment may need to be extended, sometimes to as long as 2 years, in order to fully cure the patient of infectious bacteria. However, poor compliance with such a long, complex and unpleasant combination of drugs results in a significant treatment failure rate. Worse still, resistance may emerge to these first-line agents, and thereafter to a wide range of second-line anti-mycobacterials. Not only are multi-drug resistant-TB (MDR-TB) strains difficult to treat but these strains are also life threatening, sometimes resulting in a high mortality rate (e.g., 72 to 89%) in a short period of time (e.g., 4 to 6 weeks)[6]. In general, treating individuals infected with MDR-TB is expensive, intolerable in toxicity, and frequently unsuccessful. Treatment of drug susceptible TB costs about $2,000 per patient, whereas the cost increases to as much as $250,000 per case for MDR-TB[7]. In late 1998, FDA approved a new drug rifapentine, a derivative of rifampin, the first anti-TB drug to be approved in 25 years[8]. Although TB relapse rate for rifapentine is slightly higher (10%) than that for rifampin (5%), FDA approved the new medication because it only has to be taken once weekly during the last four months of treatment, as opposed to twice weekly for rifampin.

Currently, there is no standard optimal antimicrobial therapy in AIDS patients and no single agent that is active against both infections. Challenges of management of TB in patients with AIDS are significantly higher than that in patients without AIDS. The first challenge is the pill burden. DOTS program for TB requires a patient to take 10 to 12 pills a day and the recommended highly active antiretroviral therapy (HAART) for HIV infection normally adds no less than another 20 pills. All the medications have to be taken daily, around the clock, with or without food restrictions, creating a tremendously difficult drug regimen for the patient. The second challenge is the interactions between the drugs for TB and HIV infections, which may lead to regimen intolerance and/or contraindication and add more difficulties in the treatment design. For example, rifampin is not recommended for concurrent use with almost all the anti-HIV NNRTIs and protease inhibitors, due to their contraindicated interactions.

It is clear that there is an urgent need for anti-TB drugs with improved properties such as enhanced activity against MDR strains, reduced toxicity, shortened duration of therapy, rapid mycobactericidal mechanism of action, ability to penetrate host cells and exert antimycobacterial effect in the intracellular environment.

It is an object of this invention to provide for the design, synthesis and evaluation of a library of pyranocoumarin analogues, with an ultimate goal of developing a novel anti-TB drug which should maintain the same unique resistance profile and unique mechanism of action as demonstrated by (+)-calanolide A but have improved potency.

It is another objective of this invention to further understand the structural features of pyranocoumarin necessary for the unique anti-TB activity. The compounds of the present invention are useful tool to study a structure-activity relationship (SAR), to select and/or design other molecules to inhibit and/or kill M. tuberculosis. In addition, the instant compounds of the present invention are useful tools and/or reagents to identify and validate novel targets in the life cycle of M. tuberculosis for anti-TB drug development. Furthermore, the instant compounds of the present invention can be used to probe the mechanism of actions for anti-TB agents.

SUMMARY OF THE INVENTION

The present invention provides for compounds according to formula I, compositions comprising the compounds of formula I, and methods for treating a patient who has a condition or disease associated with Mycobacterium infection and who is in need of such treatment which comprises administration of a therapeutically effective amount of at least one compound of formula I:

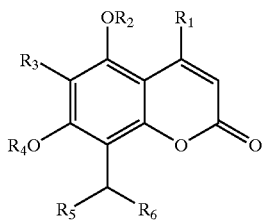

(I)

wherein $R_1$ is alkyl, alkenyl, alkynyl, aryl, OH, or $NH_2$;

$R_2$ is selected from H, alkyl, alkenyl, alkynyl, aryl, and can optionally form a 4 to 7-membered ring with $R_3$;

$R_3$ is selected from H, alkyl, alkenyl, alkynyl, aryl, and can optionally form a 4 to 7-membered ring with $R_2$;

$R_4$ is selected from H, alkyl, alkenyl, alkynyl, aryl, and can optionally form a 4 to 7-membered ring with $R_5$;

$R_5$ is selected from H, alkyl, alkenyl, alkynyl, aryl, and can optionally form a 4 to 7-membered ring with $R_4$; and $R_6$ is selected from the group consisting of =O, OH, =NH, $NH_2$, SH, $P(O)_nH_m$ substituted imines, and substituted amines, wherein n is 2–4 and m is 1–3;

The invention also provides a method for the reductive amination of a ketone comprising contacting the ketone with a compound of the formula $R'NH_2$, wherein R' is selected from the group consisting of H, alkyl, alkenyl, alkynyl, and aryl.

DETAILED DESCRIPTION OF THE PREFERRED EMBODIMENTS

BRIEF DESCRIPTION OF THE FIGURES

FIG. 1 discloses the structures of several pyranocoumarin compounds. The ring nomenclature (i.e. rings A, B, and C) as well as the numbering scheme are provided for (+)-calanolide-A (1).

FIG. 2 discloses several of the structural features in the pyranocoumarins thought to be important in modulating anti-TB activity, and also provides the generic structures of four general types of compounds (I–IV) of the invention.

FIG. 3 discloses several pyranocoumarin compound analogues.

DEFINITIONS

As used herein the terms "Mycobacterium" is taken to mean any strain of bacteria classified as Mycobacterium. In certain contexts, particular strain(s) of Mycobacterium include, but are not limited to, *Mycobacterium avium* complex (MAC), *Mycobacterium kansaii*, *Mycobacterium marinum*, *Mycobacterium phlei*, *Mycobacterium ulcerans*, *Mycobacterium xenopi*, *Mycobacterium gordonae*, *Mycobacterium terrae* complex, *Mycobacterium haemophilum*, *Mycobacterium fortuitum*, *Mycobacterium tuberculosis*, *Mycobacterium laprae*, *Mycobacterium scrofulaceum* and *Mycobacterium smegmatis*.

As used herein, the terms "conditions related to infection by Mycobacterium" or "diseases related to infection by Mycobacterium" are taken to mean any disease or condition recognized as being caused by, or further exacerbated by, an infection by Mycobacterium, as defined above.

As used herein, "alkyl", "lower alkyl", or "$C_{1-6}$ alkyl" is meant to include a straight or branched hydrocarbon having from 1 to 12 carbon atoms and includes, for example, methyl, ethyl, n-propyl, isopropyl, n-butyl, sec-butyl, isobutyl, tert-butyl, n-pentyl, n-hexyl, and the like.

As used herein, "alkenyl" means an alkyl group of 2 to 12 carbon atoms, wherein at least one carbon-carbon single bond is replaced by a carbon-carbon double bond. Examples of such groups include ethylene, 1-propene, 2-propene, 1-butene, 2-butene, isobutene, and the isomers of pentene and hexene and the like. All cis- and trans-isomers are included in the scope of the definition.

As used herein, "alkynyl" means an alkyl group of 2 to 12 carbon atoms, wherein at least one carbon-carbon single bond is replaced by a carbon-carbon triple bond. Examples of such groups include acetylene, 1-propyne, 2-propyne, 1-butyne, 2-butyne, 3-butyne, and the isomers of pentyne and hexyne and the like.

All of alkyl, alkenyl, and alkynyl groups can be optionally substituted with one or more substituent listed below for aryl, on any carbon atom that results in a stable structure that is available by conventional synthetic methods.

The term "aryl" means an aromatic carbocyclic or heterocyclic group having a single ring (e.g., phenyl, pyridine, or thiophene), multiple rings (e.g., biphenyl, indole, or benzoimidazole), or multiple condensed rings in which at least one is aromatic (e.g., 1,2,3,4-tetrahydronaphthyl, naphthyl, anthracyl, phenanthryl, or 1,2-dihydroindole), unsubstituted or substituted by 1 to 4 substituents selected from alkyl, O-alkyl (alkoxy) and S-alkyl, OH, SH, —CN, halogen, 1,3-dioxolanyl, $CF_3$, $NO_2$, $NH_2$, $NHCH_3$, $N(CH_3)_2$, NHCO-alkyl, —$(CH_2)_mCO_2H$, —$(CH_2)_mCO_2$-alkyl, —$(CH_2)_mSO_3H$, —NH alkyl, —N(alkyl)$_2$, —$(CH_2)_m$ $PO_3H_2$, —$(CH_2)_mPO_3(alkyl)_2$, —$(CH_2)_mSO_2NH_2$, and —$(CH_2)_mSO_2NH$-alkyl wherein alkyl is defined as above and m is 0, 1, 2, or 3.

By "alkoxy", "lower alkoxy" or "$C_{1-6}$ alkoxy" in the present invention is meant straight or branched chain alkoxy groups having 1–6 carbon atoms, such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy and the like.

As used herein, "4 to 7-membered ring" is meant to include an aromatic or non-aromatic ring having, zero, one, or two carbon-carbon double bonds, and optionally containing one to two heteroatoms selected from the group consisting of nitrogen, oxygen, and sulfur, which are stable and available by conventional chemical synthesis. Preferred rings comprise heterocyclic 6-membered rings, including those that contain a single oxygen atom, and optionally comprise no carbon-carbon double bonds, or a single carbon-carbon double bond.

Recently, through the Tuberculosis Antimicrobial Acquisition & Coordinating Facility (TAACF) screening program sponsored by the National Institute of Allergy and Infectious Diseases (NIAID), (+)-calanolide A (1 in FIG. 1) was found to be active against TB. (+)-Calanolide A, a natural product originally isolated from the rain forest tree *Calophyllum lanigerum*, has been previously identified to be an anti-HIV agent and it is currently undergoing clinical trials for HIV infection.

Against H37Rv strain of *M. tuberculosis* in BACTEC 12B medium using the BACTEC 460 radiometric system, (+)- calanolide A demonstrated greater than 96% inhibition at a concentration of 12.5 µg/mL. The minimum inhibitory concentration (MIC) for (+)-calanolide A, defined as the lowest concentration inhibiting 99% of the inoculum, was then determined to be 3.13 µg/mL or 8 µM. The MIC value suggests that activity of (+)-calanolide A against TB might be marginal. For comparison, MICs for the first line anti-TB drugs are 0.025–0.05 µg/mL for isoniazid, 0.005–0.2 µg/mL for rifampin, and 0.4–10 µg/mL for ethambutol. However, in a bone marrow-derived murine macrophage model, the BC 99 value of (+)-calanolide A, a concentration at which 99% of the inoculum of *M. tuberculosis* is destroyed, was 1.1 µg/mL (3 µM) against strain Erdman (TMCC 107/ATCC 35801) and 1.8 µg/mL (5 µM) against strain CSU 93 (CDC-95-031551), compared to 0.7–0.8 µg/mL (5–6 µM) for the positive control drug isoniazide. The drug inhibition patterns observed in this study led to the belief that (+)-calanolide A was a bactericidal agent. In addition, (+)-calanolide A was weakly active against *M. avium*, exhibiting 81% inhibition at a concentration of 12.5 µg/mL.

More importantly, (+)-calanolide A was active against all the first-line anti-TB drug resistant strains. As indicated in Table 1, (+)-calanolide A did not lose activity toward strains of *M. tuberculosis*, which are resistant to isoniazid, rifampin, streptomycin, and ethambutol, respectively.

In the preliminary mechanistic studies, the effect of (+)-calanolide A on the *M. tuberculosis*' synthesis of protein, RNA, DNA and lipid was assessed by measuring incorporation of appropriate radiolabeled precursors into mycobacterial macromolecular components. It was apparent that (+)-calanolide A inhibited all these biological events at a concentration of 8× MIC (64 µg/mL). However, the pattern of its inhibition was somewhat different from the respective positive control drug. For instance, the effect of (+)-calanolide A on the protein synthesis of *M. tuberculosis* occurred earlier than that observed with the positive control streptomycin (32% inhibition at 2 hours vs 43% at 5 hours). Streptomycin is a known inhibitor of protein synthesis by binding to the 30S ribosomal subunit and subsequently "freezing" the initiation complex. The fact that the inhibition pattern observed for (+)-calanolide A was different from streptomycin suggests that (+)-calanolide A may affect a target that ultimately, but not directly, affects protein synthesis. (+)-Calanolide A inhibited RNA synthesis to the extent and in the time frame very similar to the positive control rifampin, a known inhibitor of DNA dependent RNA polymerase. Also, (+)-calanolide A appears to inhibit both DNA and lipid syntheses. Approximately 77% of DNA synthesis was inhibited in a period of 3 hours while 99% of lipid synthesis was inhibited when measured at 12-hour time point. However, these inhibitions should be viewed with some reservation as DMSO at a concentration equivalent to that used to dissolve (+)-calanolide A showed 24% and 51% inhibition, respectively, of DNA synthesis and lipid synthesis during the same sampling time point.

Based on the data presented above, it appears that the effect of (+)-calanolide A on TB was more similar to rifampin than other agents. However, (+)-calanolide A is active against rifampin-resistant strain, suggesting that both compounds may affect the same biological event (RNA synthesis) but involve different targets. The inhibitory effect of (+)-calanolide A on protein and lipid syntheses is probably secondary since the target affected proceeds these biological events. It is therefore not surprising that both isoniazid- and streptomycin-resistant strains are susceptible to (+)-calanolide A (Table 1). Clearly, (+)-calanolide A represents a novel pharmacophore for anti-TB activity.

Encouraged by the (+)-calanolide A results, seven (7) other anti-HIV-1 active pyranocoumarin compounds (see FIG. 1 for structures) were also screened for anti-TB activity. Interestingly, compounds 2–5 were all determined to be active against H37Rv strain of *M. tuberculosis*, with MIC values at the same level of (+)-calanolide A, as shown in Table 2. However, compounds 6–8 were weakly active, since they only exhibited 43 to 78% inhibition at a concentration of 12.5 µg/mL.

TABLE 1

Activity of (+)-Calanolide A against anti-TB Drug Resistant Strains

| | MIC (µg/mL) (fold resistance) | | | | |
|---|---|---|---|---|---|
| Strains | (+)-Calanolide A | Isoniazid | Rifampin | Streptomycin | Ethambutol |
| H37Ra | 16 | 0.063 | ND | ND | 4 |
| H37Rv | 8 | 0.031 | 0.016 | 0.25 | 2 |
| 1369 | 8 (1) | 0.031 (1) | 64 (4,000) | 0.25 (1) | 2 (1) |
| 1371 | 8 (1) | 0.031 (1) | 0.016 (1) | >128 (>512) | 2 (1) |
| 1348 | 8 (1) | >128 (>4100) | 0.031 (2) | 0.25 (1) | 8 (4) |
| 1356 | 8 (1) | 0.25 (8) | 0.031 (2) | 0.25 (1) | 64 (32) |

TABLE 2

Activity of Pyranocoumarin Compounds against Strain H37Rv of *M. tuberculosis*

| Compound | % Inhibition | MIC (µg/mL) | $IC_{50}$ (µg/mL) | SI ($IC_{50}$/MIC) |
|---|---|---|---|---|
| (+)-Calanolide A (1) | 96 | 3.13 | 7.60 | 2.43 |
| (−)-Calanolide A (2) | 98 | 6.25 | >10 | >1.6 |
| (−)-Calanolide B (3) | 99 | 6.25 | — | — |
| Soulattrolide (4) | 99 | 3.13 | — | — |
| 7,8-Dihydrosoulattrolide (5) | 99 | 6.25 | — | — |
| (+)-12-Oxocalanolide A (6) | 78 | >12.5 | — | — |
| (±)-6 | 59 | >12.5 | — | — |
| (±)-7,8-Dihydro-12-Oxocalanolide A (7) | 43 | >12.5 | — | — |
| (+)-Calanolide D (8) | 57 | >12.5 | — | — |

The results reported above reveal a few key features of structural requirements for these pyranocoumarins to exert their anti-TB activity. First of all, the 12-OH group appears to be the single most important structural element, since compounds with such a group as in 2–5 are active while those without, as in 6–8, which all possess a carbonyl group at the 12-position, are inactive. In contrast to the anti-HIV activity,[1] however, the stereochemistry of the 12-OH group in these pyranocoumarins may not be critical for anti-TB activity because (−)-calanolide A (2), possessing the 12-OH group in the β position, was as active against TB as (+)-calanolide A (1) and compounds 3–5, which all have a 12-OH group in the α position. Furthermore, it is apparent that the coumarin (Ring A, see the ring designation in FIG. 1) and chromene (Ring B) rings are flexible to modifications. For example, either replacement of the n-propyl group in 3 with a phenyl, resulting in 4, or saturation of the double bond in Ring B of 4, leading to 5, still maintains the anti-TB activity. However, the necessity of methyl groups in the chroman ring (Ring C) is not clear. Therefore, the structural features in the pyranocoumarins required for anti-TB activity can be summarized by structure I as shown in FIG. 2.

In one embodiment, the invention provides for compounds of formula I or pharmaceutically acceptable salts thereof:

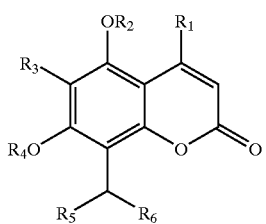

(I)

wherein $R_1$ is alkyl, alkenyl, alkynyl, aryl, OH, or $NH_2$;

$R_2$ is selected from H, alkyl, alkenyl, alkynyl, aryl, and can optionally form a 4 to 7-membered ring with $R_3$;

$R_3$ is selected from H, alkyl alkenyl, alkynyl, aryl, and can optionally form a 4 to 7-membered ring with $R_2$;

$R_4$ is selected from H, alkyl, alkenyl, alkynyl, aryl, and can optionally form a 4 to 7-membered ring with $R_5$;

$R_5$ is selected from H, alkyl, alkenyl, alkynyl, aryl, and can optionally form a 4 to 7-membered ring with $R_4$; and $R_6$ is selected from =O, =NH, OH, $NH_2$, NRH, NR, SH, and $P(O)_nH_m$, wherein n is 2–4 and m is 1–3.

In one embodiment, this invention provides for methods for treating a patient who has a condition or disease related to Mycobacterium infection and who is in need of such treatment which comprises administration of a therapeutically effective amount of at least one compound of formula I or a pharmaceutically acceptable salt thereof:

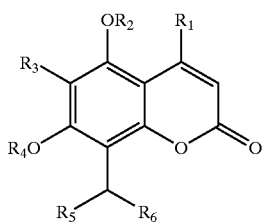

(I)

wherein $R_1$ is alkyl, alkenyl, alkynyl, aryl, OH, or NH2;

$R_2$ is selected from H, alkyl, alkenyl, alkynyl, aryl, and can optionally form a 4 to 7-membered ring with $R_3$;

$R_3$ is selected from H, alkyl, alkenyl, alkynyl, aryl, and can optionally form a 4 to 7-membered ring with $R_2$;

$R_4$ is selected from H, alkyl, alkenyl, alkynyl, aryl, and can optionally form a 4 to 7-membered ring with $R_5$;

$R_5$ is selected from H, alkyl, alkenyl, alkynyl, aryl, and can optionally form a 4 to 7-membered ring with $R_4$; and $R_6$ is selected from the group consisting of =O, OH, =NH, $NH_2$, SH, $P(O)_nH_m$ substituted imines, and substituted amines, wherein n is 2–4 and m is 1–3;

In an embodiment, this method of treatment can be used where the disease is tuberculosis.

In an embodiment, this method of treatment can be used where the disease is tuberculosis associated with an immunodeficiency including, but not limited to, human immunodeficiency virus (HIV) infection, acquired immune deficiency syndrome (AIDS), or AIDS related complex (ARC).

In an embodiment, this method of treatment can be used to treat a condition or disease related to an existing Mycobacterium infection.

In an embodiment, this method of treatment can be used to prevent Mycobacterium infection, for example, in a patient with a compromised immune system.

In preferred embodiments, this method of treatment can be used to treat or prevent Mycobacterium infection, especially when the Mycobacterium is *Mycobacterium tuberculosis*.

The compounds of the invention may be formulated as a solution of lyophilized powders for parenteral administration. Powders may be reconstituted by addition of a suitable diluent or other pharmaceutically acceptable carrier prior to use. The liquid formulation is generally a buffered, isotonic, aqueous solution. Examples of suitable diluents are normal isotonic saline solution, standard 5% dextrose in water or in buffered sodium or ammonium acetate solution. Such formulation is especially suitable for parenteral administration, but may also be used for oral administration. It may be desirable to add excipients such as polyvinylpyrrolidone, gelatin, hydroxy cellulose, acacia, polyethylene glycol, mannitol, sodium chloride or sodium citrate.

Alternatively, the compounds of the present invention may be encapsulated, tableted or prepared in an emulsion (oil-in-water or water-in-oil) syrup for oral administration. Pharmaceutically acceptable solids or liquid carriers, which are generally known in the pharmaceutical formulary arts, may be added to enhance or stabilize the composition, or to facilitate preparation of the composition. Solid carriers include starch (corn or potato), lactose, calcium sulfate dihydrate, terra alba, croscarmellose sodium, magnesium stearate or stearic acid, talc, pectin, acacia, agar, gelatin, maltodextrins and microcrystalline cellulose, or colloidal silicon dioxide. Liquid carriers include syrup, peanut oil, olive oil, corn oil, sesame oil, saline and water. The carrier may also include a sustained release material such as glyceryl monostearate or glyceryl distearate, alone or with a wax. The amount of solid carrier varies but, preferably, will be between about 10 mg to about 1 g per dosage unit.

The dosage ranges for administration of the compounds of the invention are those to produce the desired affect whereby symptoms of infection are ameliorated. For example, as used herein, a pharmaceutically effective amount for a mycobacterium infection refers to the amount administered so as to maintain an amount which suppresses or inhibits mycobacterium infection as evidenced by standard assay(s). The dosage will also be determined by the existence of any adverse side effects that may accompany the compounds. It is always desirable, whenever possible, to keep adverse side effects to a minimum.

One skilled in the art can easily determine the appropriate dosage, schedule, and method of administration for the exact formulation of the composition being used in order to achieve the desired effective concentration in the individual patient. However, the dosage can vary from between about 0.001 mg/kg/day to about 50 mg/kg/day, but preferably between about 0.01 to about 20 mg/kg/day.

The pharmaceutical composition may contain other pharmaceuticals in conjunction with the compounds of the invention for use in combination therapy. For example, other pharmaceuticals may include, but are not limited to, other antiviral compounds (e.g., AZT, ddC, ddI, D4T, 3TC, acyclovir, gancyclovir, fluorinated nucleosides and non-nucleoside analog compounds such as TIBO derivatives and nevirapine, α-interfon and recombinant CD4), protease inhibitors (e.g., indinavir, saquinavir, ritonavir, and nelfinavir), immunomodulators such as, for example, immunostimulants (e.g., various interleukins and cytokines), antibiotics (e.g., antimicrobials such as the anti-TB agents isoniazid, rifampin, rifabutin, rifapentine, pyrazinamide, and ethambutol, as well as antibacterial, antifungal, antipneumocysitis agents), and chemokine inhibitors. Administration of the inhibitory compounds with anti-retroviral agents that act against other HIV proteins such as protease, intergrase and TAT will generally inhibit most or all replicative stages of the viral life cycle.

The compounds described herein can be used either alone or in conjunction with other pharmaceutical compounds to combat multiple infections. For example, the compounds of the invention can be used either alone or combined with acyclovir in a combination therapy to treat HSV-1; with one or more anti-mycobacterial agents such as anti-TB agents such as Isoniazid, rifamycins (e.g., rifampin, rifabutin and rifapentine), pyrazinamide, and ethambutol as a prophylatic or therapeutic treatment; in combination with Intron A and/or a biflavanoid for treating Hepatitis B; with gancyclovir, progancyclovir, famcyclovir, foscarnet, vidarabine, cidovir, and/or acyclovir for treating herpes viruses; and with ribavarin, amantidine, and/or rimantidine for treating respiratory viruses.

In another embodiment the present invention relates to a method of stepwise reductive amination of a ketone comprising the steps of:
(a) contacting the ketone with a solution comprising an amount of a compound of the formula R'NH$_2$,
 wherein R' is selected from the group consisting of H, alkyl, alkenyl, alkynyl, and aryl under conditions that allow formation of an imine intermediate compound; and
(b) contacting the imine intermediate compound generated in step (a) with an amount of a reducing agent sufficient to reduce the imine intermediate compound to its amino analog, under conditions that allow reduction of the imine intermediate compound to its amino analog.

In one embodiment, the amount of R'NH$_2$ ranges between 1 to 500 molar equivalents relative to the amount of ketone to be reduced. Use of excessive amount of R'NH$_2$ tends to shorten the reaction time for the intermediate imine formation as well as drive the reaction to completion. In preferred embodiments, the method comprises 30 to 70 molar equivalents of ammonia (R' is H) or 10 to 40 molar equivalents of amine compound (i.e. R' is not H).

In preferred embodiments the solvents used in the method are alcohols and ethers including, but not limited to, methanol, ethanol, propanol, isopropanol, butanol, ethyl ether, methyl t-butyl ether, dioxane, tetrahydrofuran, diglyme, tetraglyme, and the like. Compounds of formula R'—NH$_2$ can either be added to the solution comprising the ketone, or can be present in the solution to which the ketone is added. In preferred embodiments, the ketone compound is added to the solution comprising the compound R'NH$_2$.

The compound of formula R'NH$_2$ can be added to the solvent by any method known in the art including, but not limited to, bubbling of gas phase R'NH$_2$ through the solvent, or by addition of liquid R'NH$_2$ to the solvent.

In one embodiment, this step of the method can be carried out at −78 to 120° C. In preferred embodiments, the reaction temperature is about room temperature.

In one embodiment, the reducing agents comprise common reducing agents capable of reducing an imine to an amine, and are known to those of skill in the art. Examples of such reducing agents include, but are not limited to, LiAlH$_4$, (i-Bu)$_2$AlH, (n-Bu)$_3$SnH, NaBH$_3$CN, NaB(OAc)$_3$H, LiBH$_4$, NaBH$_4$, Zn(BH$_4$)$_2$, BH$_3$, or a borane compound such as 9-BBN and DIP-chloride. The imine intermediate can be isolated and purified before it is reduced, or the imine intermediate can be reduced without substantial purification. In preferred embodiments, the reduction is performed on the crude product, without substantial purification. The reaction can be carried out at −78 to 120° C. In preferred embodiments, the reaction temperature is about room temperature.

In one embodiment, the method further comprises a metal additive, added at the step including the reducing agent. Examples of metal additives include, but are not limited to, CeCl$_3$, ZnCl$_2$, AlCl$_3$, TiCl$_4$, SnCl$_3$, and LnCl$_3$.

In one embodiment the amount of reducing agent used ranges from 0.1 to 50 molar equivalents.

In a preferred embodiment, the reducing agent is added to the crude imine intermediate, and comprises NaBH$_4$. In an especially preferred embodiment, the added amount of NaBH$_4$ is 3 to 6 molar equivalents, relative to the amount of imine intermediate, and is carried out at about room temperature.

In another embodiment the present invention relates to a method of making compounds of formula I (R$_6$ is =NH, or substituted imines) comprising the step of: (a) contacting the ketone with a solution comprising an amount of a compound of the formula R'NH$_2$, wherein R' is selected from the group consisting of H, alkyl, alkenyl, alkynyl, and aryl, under conditions that allow formation of an imine intermediate compound.

In a preferred embodiment, the method of stepwise reductive amination is used to generate a compound of formula (I) wherein R$_6$ is NH$_2$ or RNH comprising: (a) contacting a ketone compound of formula (I) (wherein R$_6$ is =O) with an excess of a compound of the formula R'NH$_2$, under conditions that allow formation of an imine intermediate compound of formula (I) (R$_6$ is =NH or =NR); and (b) contacting the imine intermediate compound of formula (I) with an amount of a reducing agent sufficient to reduce the imine moiety of the imine intermediate compound of formula (I) to its amino analog, under conditions that allow for said reduction.

Synthesis of Compounds

One of skill in the art can identify alternative synthetic pathways that can be used to make the compounds of the instant invention. The following represents an example of one synthetic approach and should not be viewed as limiting the spirit or scope of the invention.

One synthetic approach useful in generating the compounds of the invention is to systematically modify the chromene and chroman rings (B and C of formula (II), vide infra). A number of characteristics of analogs of interest have been identified and listed in FIG. 3. Initially, a small number of compound library was designed, synthesized and tested for anti-TB activity (FIG. 3). The first three categories of compounds listed in FIG. 3 are set to further clarify the importance of Ring B and C, while the fourth category represents the corresponding amino derivatives. The amino compounds may be of particular interest because they can participate in hydrogen bonding, and is less prone to elimination under acidic conditions, relative to an OH group. Further, an amino compound tends to have an increased water-solubility, especially by forming a salt with an acid, which offers an enhanced bioavailability.

Based on the initial biological screening results, the compound library was expanded to encompass compounds selected from the structure shown below as formula (II). B and C can be open structure, or 4 to 7-membered ring, preferably a 6-membered ring, with or without substituents; X can be O, OH NH, $NH_2$, NRH, NR, SH, and $P(O)_nH_m$, wherein n is 2–4 and m is 1–3.

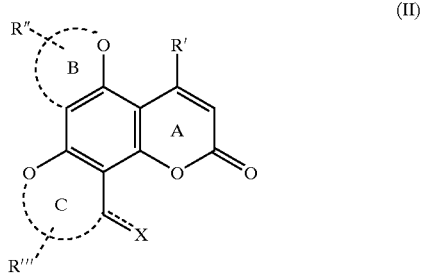

(II)

Synthesis of Type I Compounds

Type I compounds resulted from the modification on Ring C to determine if the rigidity of the ring system is required. Compound 9 can be viewed as an acyclic form of calanolide A or B, with the same number of carbon atoms as the latter molecules but with two fewer chiral centers, allowing for easy manufacture. This compound has been Synthesized previously[10] and, therefore, the reported procedures, as described in Scheme 1, are followed, starting from coumarin 28. Briefly, selective Friedel-Crafis acylation of 28 with propionic anhydride in the presence of $AlCl_3$ affords 8-acylated coumarin 29, which is then treated with 4,4-dimethoxy-2-methylbutan-2-ol to furnish 30. Alkylation of 30 with iodoethane, followed by reduction with sodium borohydride, provides 9. Hydrogenation of 9 with $NH_4OH$-poisoned $PtO_2$ as catalyst[11] affords the corresponding dihydro compound 10. Likewise, treatment of 30 with iodomethane or acetyl chrolide, followed by reduction with $NaBH_4$, provides 11b and 11d (Scheme 1). Direct reduction of 30 leads to the formation of 11a. Also, hydrogenation of 11a, 11b and 11d with $NH_4OH$-poisoned $PtO_2$ as catalyst furnishes the corresponding dihydro compound 12a, 12b and 12d, respectively. Hydrogenation of 31 yields the corresponding saturated ketone 44.

Scheme 1

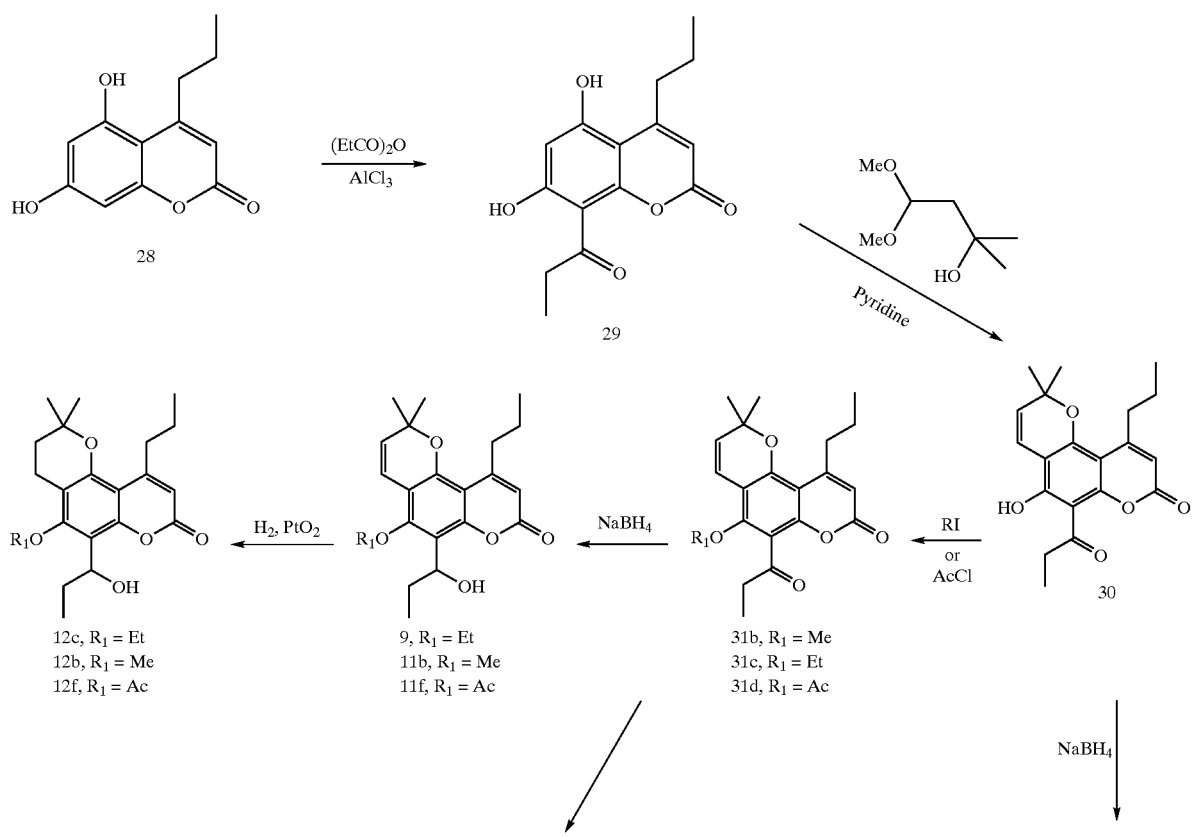

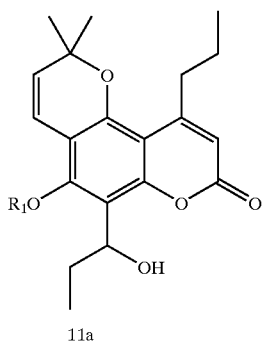

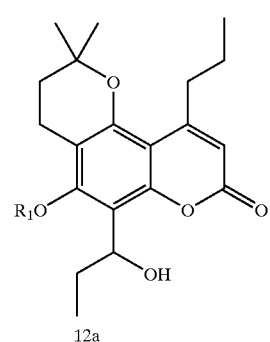

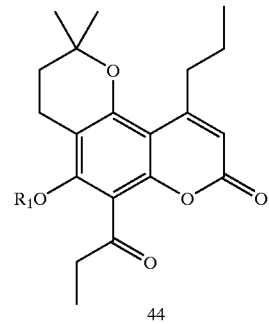

44a R₁ = H
44b R₁ = Me
44c R₁ = Et
44d R₁ = CH≡CCH
44e R₁ = HOCH₂CH₂
44f R₁ = AcOCH₂CH₂
44g R₁ = CH₂=CHCH₂
44h R₁ = i-Pr
44i R₁ = EtO₂CCH₂
44j R₁ = Ac
44k R₁ = Ts
44m R₁ = MeOCH₂

12a
12b R₁ = Me
12c R₁ = Et
12d R₁ = CH≡CCH
12e R₁ = HOCH₂CH₂

11a
11b R₁ = Me
9 R₁ = Et
11d R₁ = CH≡CCH
12e R₁ = HOCH₂CH₂

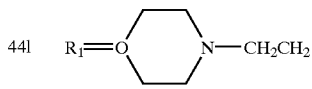

Since formylated chromeno-coumarin 33 has been reported in the literature[12], compounds 13–16 are easily prepared from this intermediate (Scheme 2). Thus, Vilsmeier reaction on coumarin 28 by treating with N-methylformanilide in the presence of POCl₃ gives 8-formylated coumarin 32.

Scheme 2

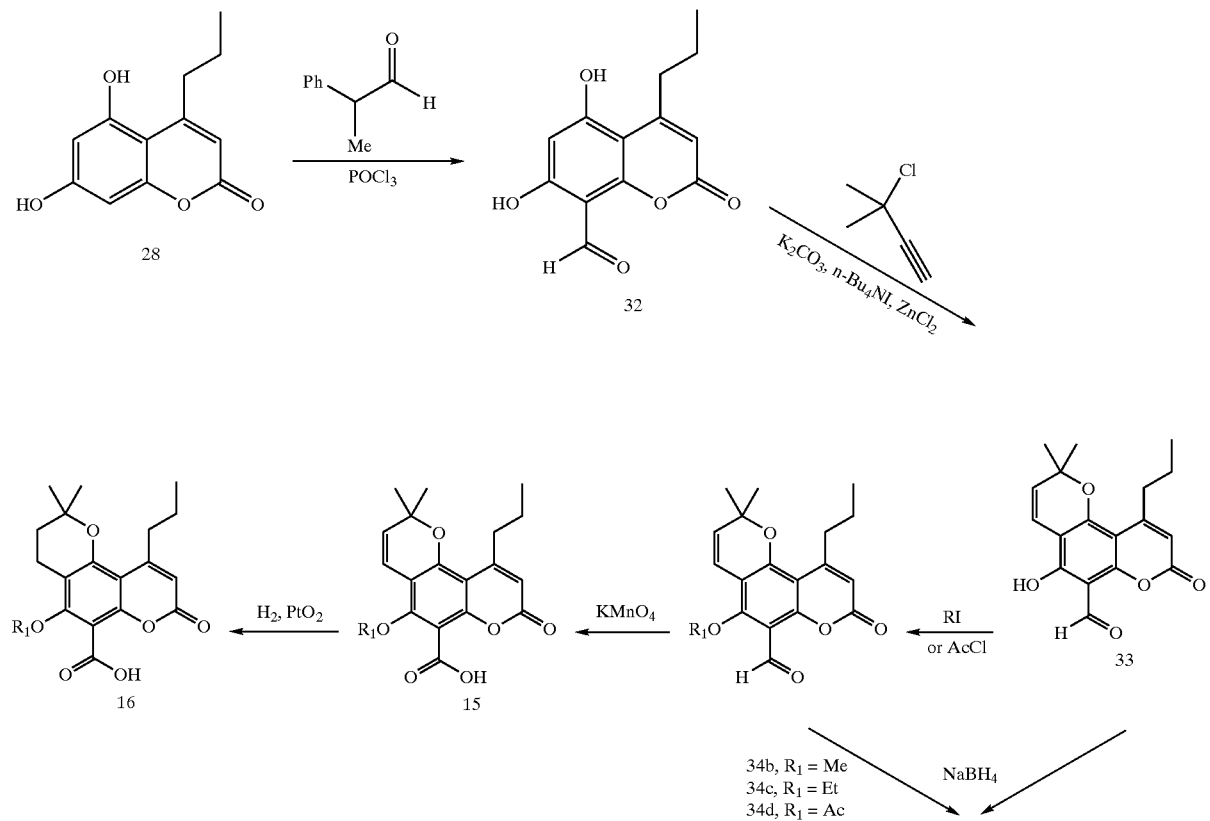

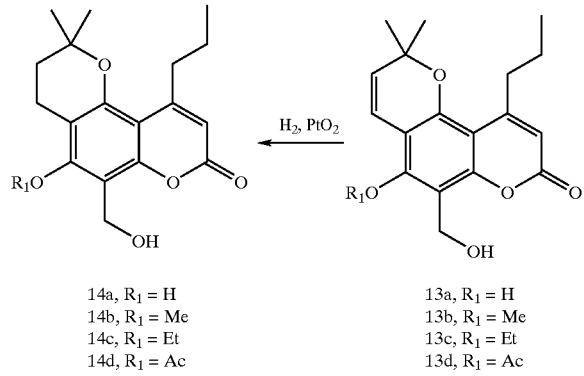

| 14a, $R_1$ = H | 13a, $R_1$ = H |
| 14b, $R_1$ = Me | 13b, $R_1$ = Me |
| 14c, $R_1$ = Et | 13c, $R_1$ = Et |
| 14d, $R_1$ = Ac | 13d, $R_1$ = Ac |

Subsequent treatment of 32 with 3-chloro-3-methyl-1-butyne in the presence of $K_2CO_3$ and n-$Bu_4$NI in DMF and 2-butenone, followed by addition of anhydrous $ZnCl_2$, produces 33. Alkylation or acylation of 33 following the similar procedures as described above affords 34. Reduction of 33 and 34 with $NaBH_4$ provides the designed compound 13a–d (Scheme 2). Oxidation of 34 with $CrO_3$ or $KMnO_4$ delivers the acid derivative 15. Once again, hydrogenation of 13a–d and 15 catalyzed by Pd/C or $PtO_2$ furnishes the corresponding dihydro compound 14a–d and 16, respectively.

Following the same chemistry described above, a number of library compounds were made by varying the substituents $R_1$, $R_2$, and $R_3$.

Synthesis of Type II Compounds

Type II compounds address the importance of Ring B by maintaining Ring C (formula II). We have previously developed a method for the synthesis of coumarino-chromanone 37a[13] and demonstrated its ready alkylation of the phenol group (Scheme 3). Therefore, 29 is readily protected by benzyl groups. The 7-benzyl group adjacent to the carbonyl function is then selectively deprotected using $BBr_3$ (1.0 equiv.), providing phenol 35. Aldol reaction with $CH_3CHO$ in the presence of $TiCl_4$ affords syn diastereomer 36 as a crystalline compound. Mitsunobu cyclization of 36, followed by debenzylation, furnishes the trans-chromanone 37a.

Alkylation of 37a using allyl bromide in DMF in the presence of $K_2CO_3$ is generally completed in a couple of hours, leading to the formation of 37c, with only trace amount of the cis isomer.[13] The alkylation of 37a is extended to other alkylating agents (RX) as specified in Scheme 3, yielding phenyl ethers 37b and 37d. Alternatively, Mitsunobu coupling of 37a with ROH forms a phenol ether bond. Reduction of 37a–d with $NaBH_4$ provides the designed compound 17a–d (Scheme 3). It is realized that both α and β isomers are formed during the reduction. However, in the presence of $CeCl_3$[14], the reduction using $NaBH_4$ results in an β form predominately.

Scheme 3

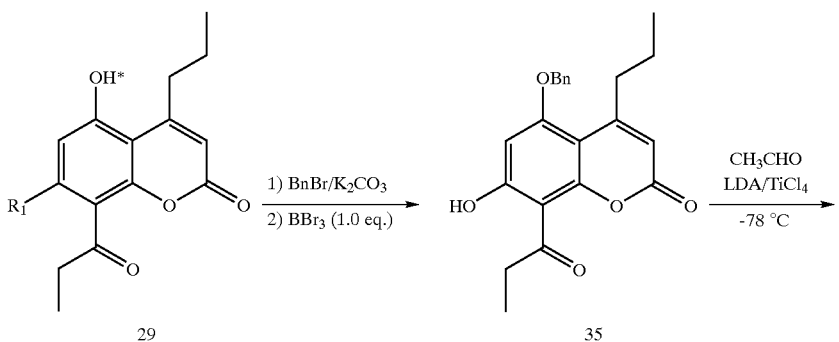

29
29a $R_1$ = H
29b $R_1$ = Me
29c $R_1$ = i-Pr
29d $R_1$ = $CH_2$=$CHCH_2$

35

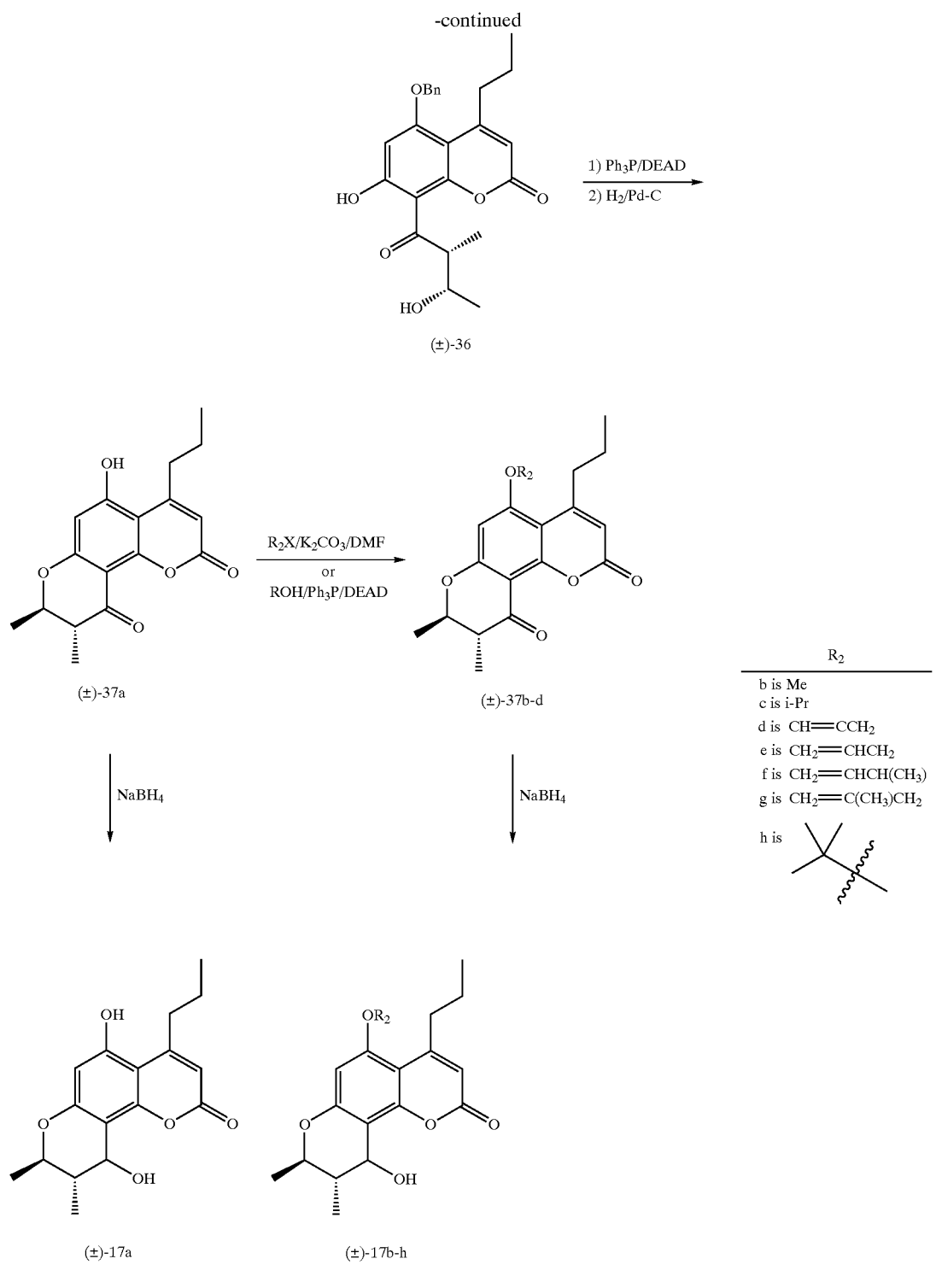

Compound 18 determined if the methyl groups in Ring C are needed. Relative to calanolide compounds, compound 18 has two less chiral centers and should be relatively easier to manufacture even if the Ring C system needs to be maintained for anti-TB activity. The synthesis of 18 is described in Scheme 4. Analogous to coumarin 29, 8-acetyl coumarin 38 is synthesized via the selective Friedel-Crafts acylation[14] of coumarin 28 with acetic anhydride in the presence of AlCl$_3$. Benzylation of 38, followed by selective debenzylation using 1.0 equiv. of BBr$_3$,[13] yields phenol 39. Treatment of 39 with paraformaldehyde in the presence of pyridinium p-totuenesulfonate (PPTS),[2] followed by debenzylation, furnished the ketone derivative 40a. Alkylation of 40a with alkylating agents in DMF in the presence of K$_2$CO$_3$, or Mitsunobu coupling with the corresponding alcoholic compounds, leads to the formation of phenyl ethers 40b–d. Reduction of 40a–d with NaBH$_4$ provides the designed compound 18a–d (Scheme 4). Once again, the α and β isomers of 18a–d are not separated for the biological screening.

Scheme 4

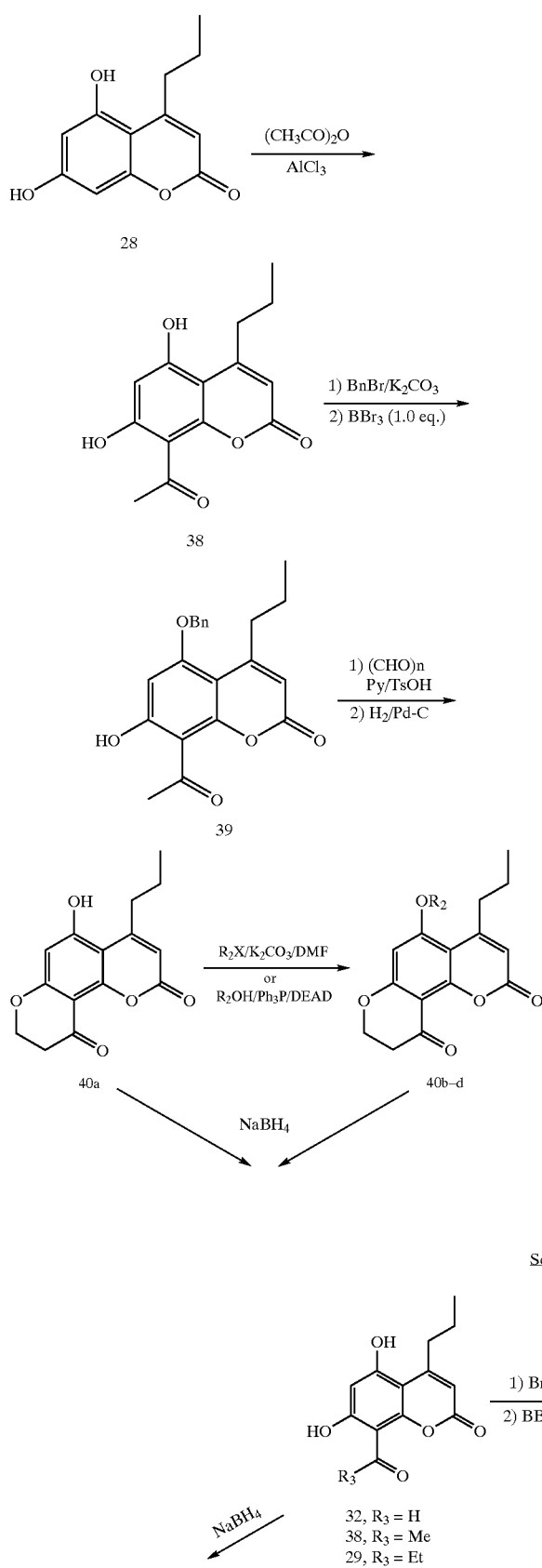

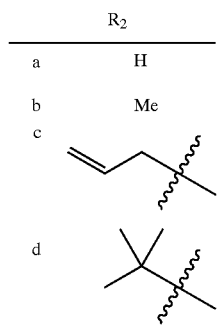

Following the same chemistry described above, a good number of library compounds are built up by varying the substituents $R_1$, $R_2$, $R_3$, and $R_4$.

Synthesis of Type III Compounds

The representative Type III compounds as identified in FIG. 3 can be synthesized via conventional medicinal chemistry approach. The first representative compound of this series is compound 19, which is a dual-acyclic form of calanolide A or B, with the same number of carbon atoms as the latter molecules. A more generalized structure, with elimination of both Ring B and Ring C, is illustrated in 21. The synthesis of these compounds is very straightforward.

Therefore, as shown in the previous schemes, 8-acylated coumarins 29, 32, and 38 are obtained by following the literature procedures. Reduction of these compounds with $NaBH_4$ affords the desired 21 ($R_1=R_2=H$, $R_3=H$, Me or Et, in Scheme 5). Benzylation of 29, 32, and 38, followed by selective debenzylation using 1.0 equiv. of $BBr_3$,[13] yields monobenzylated phenols 32, 39, and 41. Alkylation of the latter compounds with alkylating agents ($R_1X$) in DMF in the presence of $K_2CO_3$ leads to the formation of phenyl ethers 42 after debenzylation. A similar alkylation process on 42 yields 43. Reduction of 42 and 43 with $NaBH_4$ affords the designed compounds 21 (Scheme 5). Compound 19 is a special case of 21 and is prepared following the same sequence. Hydrogenation of 19 catalyzed by poisoned $PtO_2$ furnishes 20. Furthermore, oxidation of 43 ($R_3=H$) and 21 ($R_1=R_2=R_3=H$) with $CrO_3$ or $KMnO_4$ delivers the acid derivative 21 ($R_3=$carbonyl) (Scheme 5).

-continued

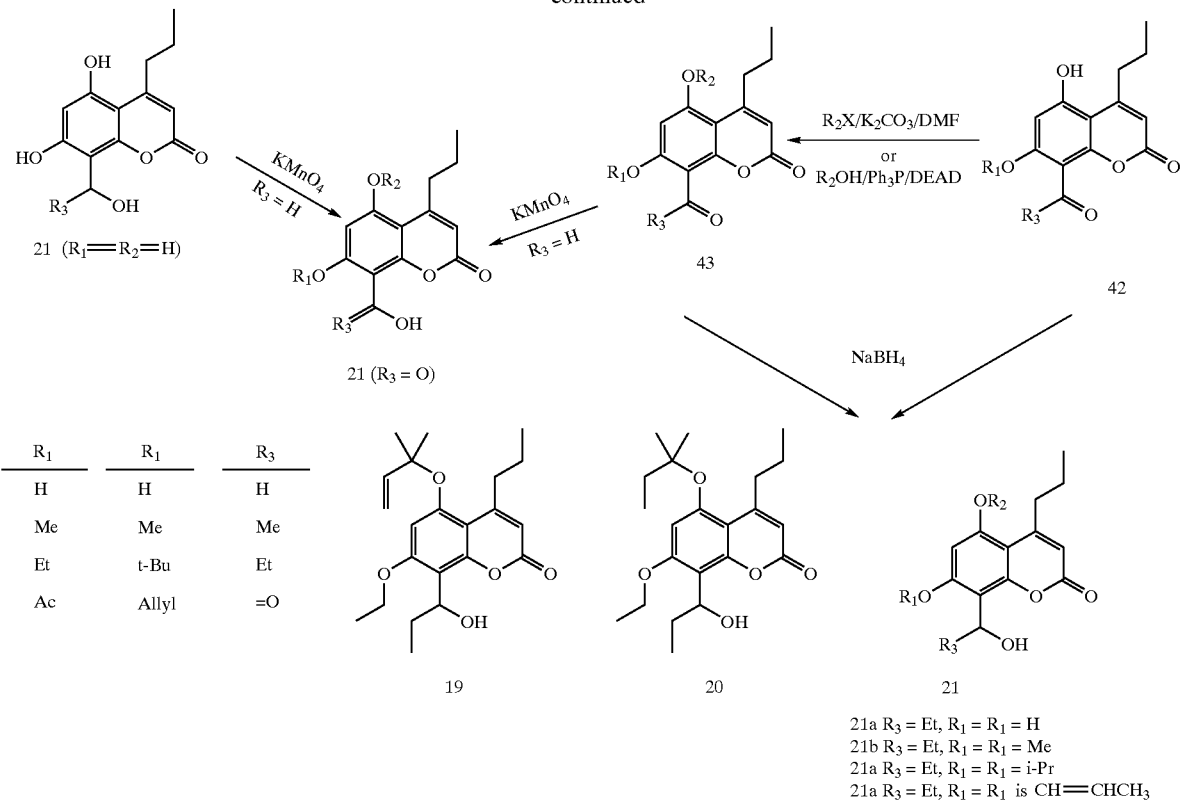

Following the same chemistry described above, a larger library of Type III compounds were investigated using either medium- or high-throughput combinatorial approaches.

Synthesis of Type IV Compounds

Type IV compounds are the amino derivatives of formula (I). As stated above, the amino compounds may be of particular interest for a number of reasons, including the ability to form hydrogen bonds and an increased water-solubility, especially by salt formation with an acid. These compounds of the invention offer an enhanced bioavailability and facilitate the future in vivo and clinical studies.

In general, amino compounds can be derived either from reductive amination from the corresponding carbonyl derivatives[16] or from direct replacement of hydroxyl group with amines[17]. Amino compound 23 is known and has been synthesized by nucleophilic displacement of the calanolide triflate ester with $NaN_3$, followed by hydrogenolysis with the poisoned $PtO_2$ catalyst. Initially, reductive amination approach is investigated. The precursor carbonyl compounds such as 12-oxocalanolide A (6), 29, 30 and 31 (Scheme 1), 32, 33 and 34 (Scheme 2), 38 and 40 (Scheme 4), as well as 42 and 43 (Scheme 5), are obtained by following the procedures described above. Reductive amination of these carbonyl compounds with $NH_4Cl$ and $NaBH_3CN$[16] affords the corresponding amino derivatives 22, 24, 26, 27 (Scheme 6). Catalytic hydrogenation of 22 and 24 provides the dihydro amino compound 23 and 25.

Scheme 6

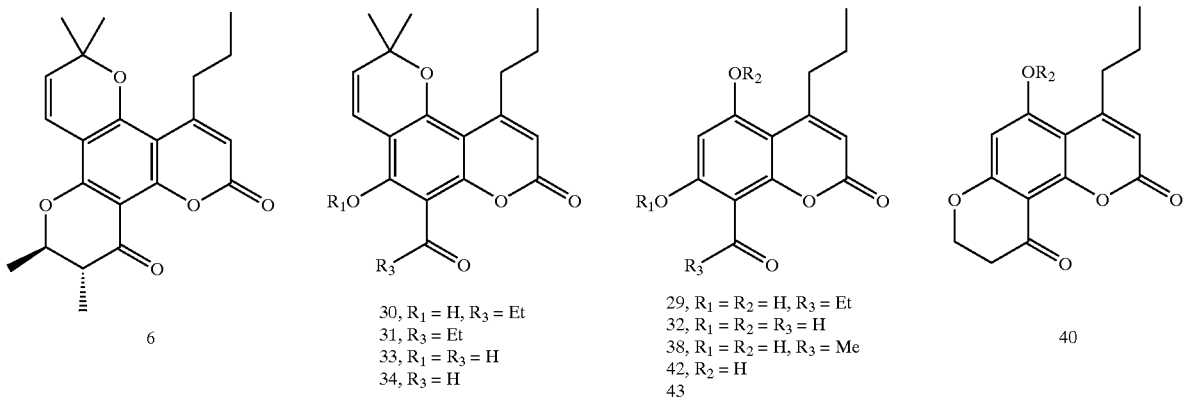

-continued
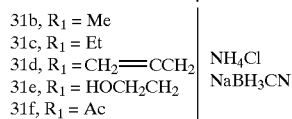
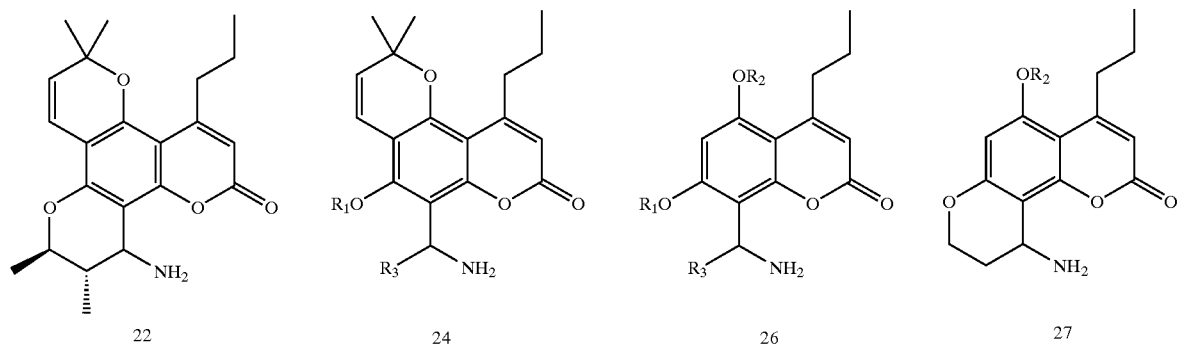
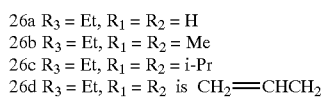
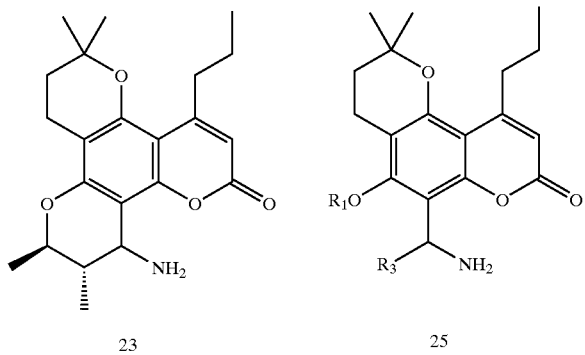
Alternatively, amino compounds 22, 24, 26, 27 are obtained by treating the corresponding alcoholic precursors with $HN_3$ in the presence of $PPh_3$ and DEAD followed by the hydrolysis[17] (Scheme 7).

Scheme 7

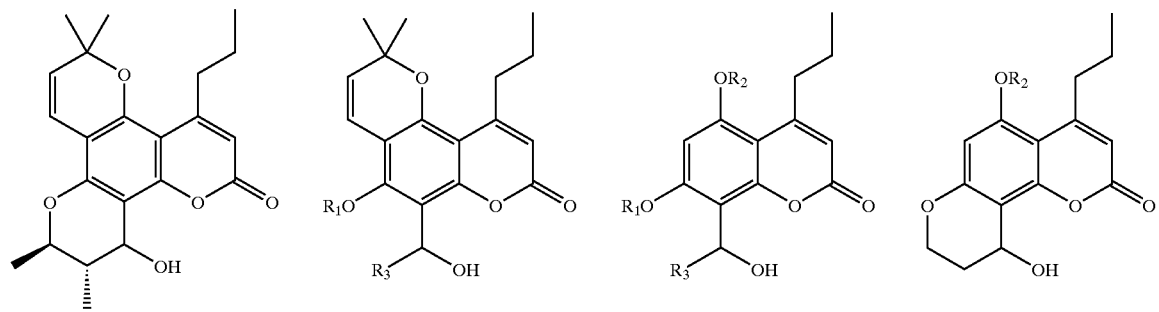

1    9–14    19–21    18

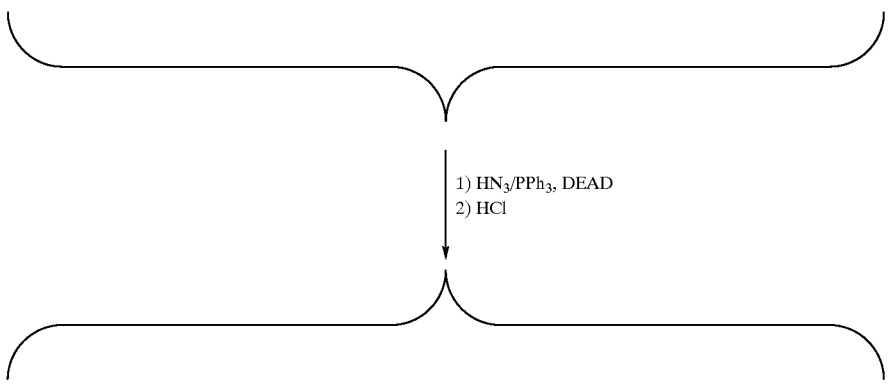

1) HN$_3$/PPh$_3$, DEAD
2) HCl

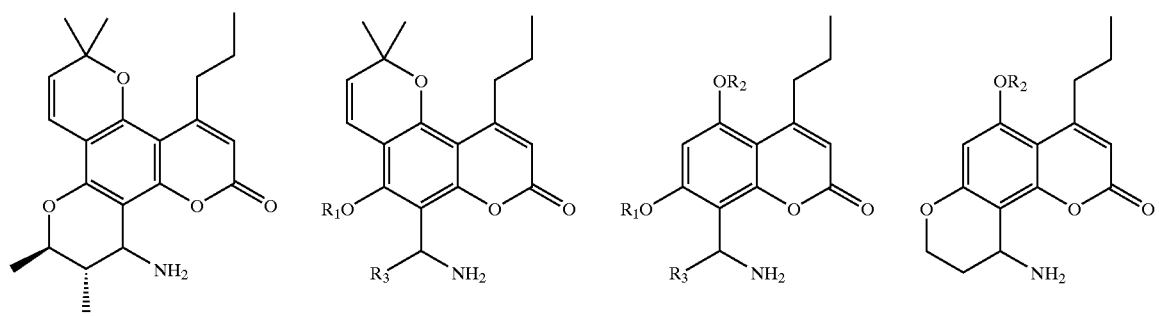

22    24    26    27

Applicants have successfully developed a one-pot stepwise red-active amination which would have a very general application. Applicants have found that the treatment of a ketone with an excessive amount of NH$_3$(g) in organic solvent led to the formation of a polar spot as shown on TLC, presumably to be the corresponding imine A (Scheme 8). $^1$H NMR on the isolated product confirmed the structure to be imine A. Reduction of imine A with NaBH$_4$ furnished the corresponding amine B. To Applicants' knowledge, this is the first time that NH$_3$(g) is utilized in the stepwise reductive amination. Furthermore, when NH$_3$(g) is replaced with amine derivatives (R'NH$_2$), the corresponding substituted amino analogues can be prepared. Thus, ketone compounds 6, 29, 30, and 31 were treated with NH$_3$(g) or amine derivatives (R'NH$_2$), followed by NaBH$_4$ reduction, affording the corresponding amino compounds 22, 45, and 46 (Scheme 8).

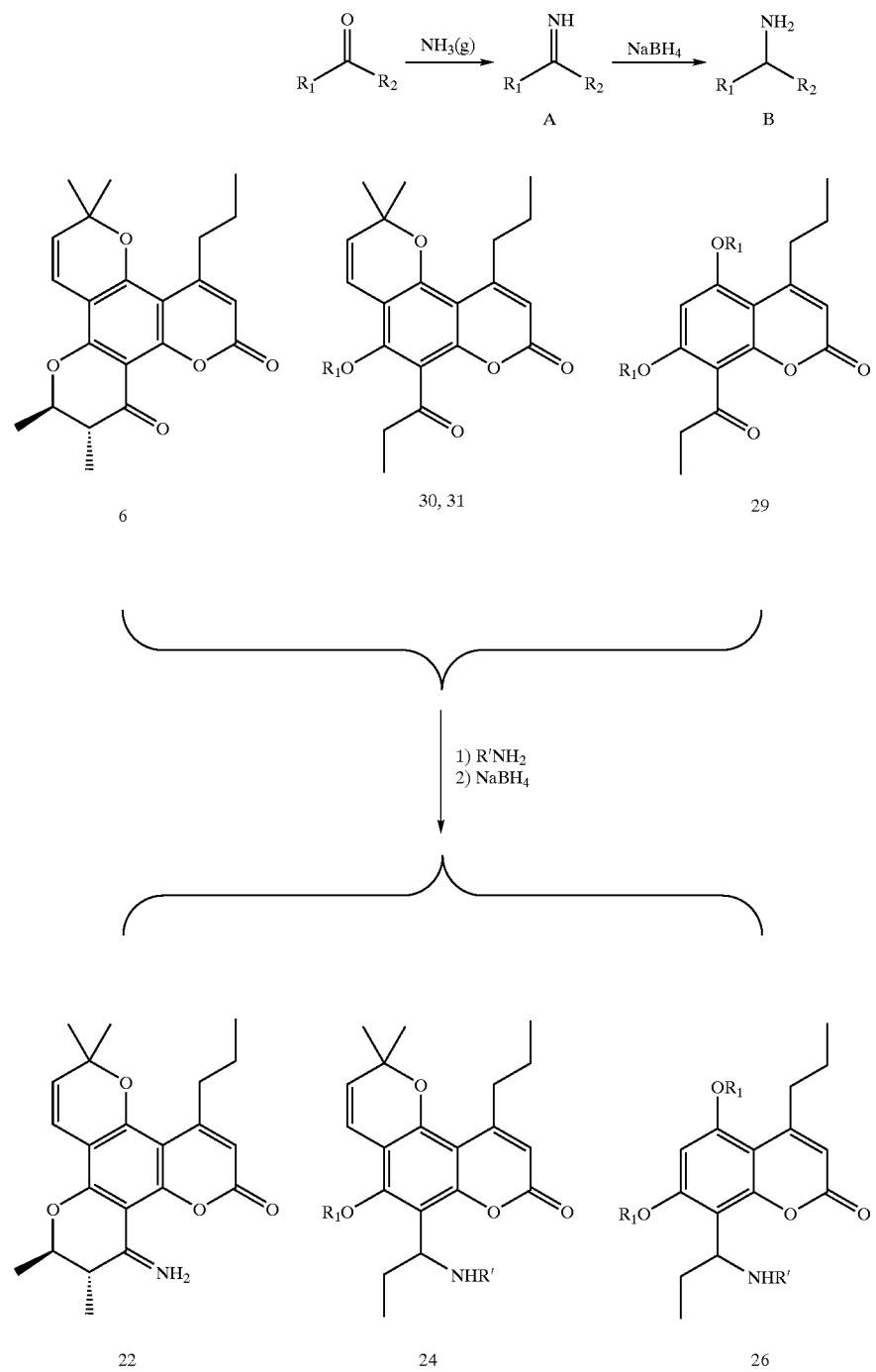

-continued

| $R_1/R'$ | 24 Yield % | 26 Yield % |
|---|---|---|
| a, H/H | | |
| b, Me/H | 98 | 60 |
| c, Et/H | | |
| d, CH≡CCH$_2$/H | | |
| e, HOCH$_2$CH$_2$/H | | |
| f, Me/Me | | |
| g, Me/Et | 27 | |
| h, Me/i-Pr | | |
| i, Me/HOCH$_2$CH$_2$ | 22 | |
| j, Me/Bn | | |
| k, i-Pr/H | | 23 |
| l, CH$_2$=CHCH$_2$/H | | 46 |
|  | | |

In order to further evaluate the flexibility of the OH group, identified to be the key structural elements required for anti-TB activity in the lead pyranocoumarin compounds, 7,8-dihydroketones 44 were synthesized (Scheme 9). Two synthetic routes have been utilized. One is the hydrogenation of 30 and 31, and the other is the direct alkylation of 44a.

Scheme 9

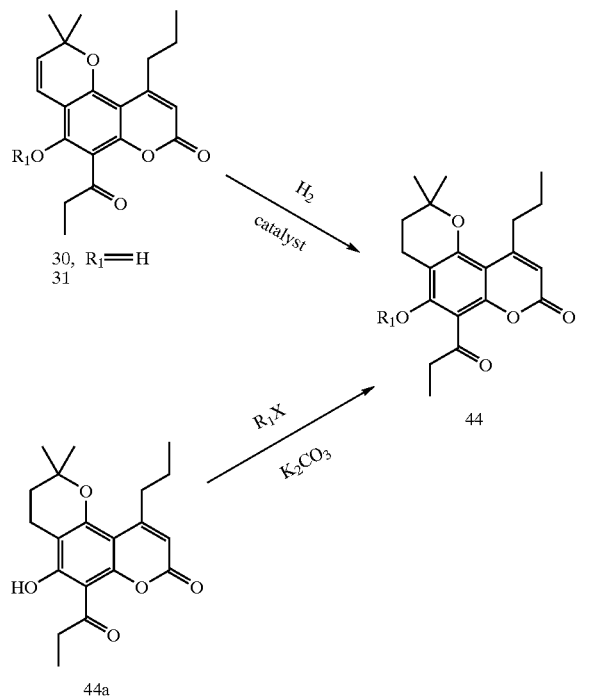

| $R_1$ | Catalyst or Reagents | Yield % |
|---|---|---|
| a, H | PtO$_2$ (NH$_3$) in toluene | |
| b, Me | 5% PtS$_x$ on C in EtOH | 68 |
| c, Et | PtO$_2$ (NH$_3$) in EtOH | 61 |
| d, CH≡CCH$_2$ | CH≡CCH$_2$Cl | 72 |
| g, CH$_2$=CHCH$_2$ | CH$_2$=CHCH$_2$Br | 93 |
| n, CH$_2$=CHCH(CH$_3$) | CH$_2$=CHCH(CH$_3$) | |
| o, CH$_2$=C(CH$_3$)CH$_2$ | CH$_2$=C(CH$_3$)CH$_2$ | |
| h, i-Pr | i-PrBr | 89 |
| f, AcOCH$_2$CH$_2$ | AcOCH$_2$CH$_2$Br | 82 |
| e, HOCH$_2$CH$_2$ | | 33 |
| m, MeOCH$_2$ | MeOCH$_2$Br | 92 |
| l, 2-(4-morpholin)-ethyl | 2-(4-morpholin)ethyl Bromide | 73 |
| i, EtO$_2$CCH$_2$ | EtO$_2$CCH$_2$Br | 81 |

EXAMPLES

The following examples are presented merely for illustrative purposes and are not intended to limit the spirit or scope of the instant invention.

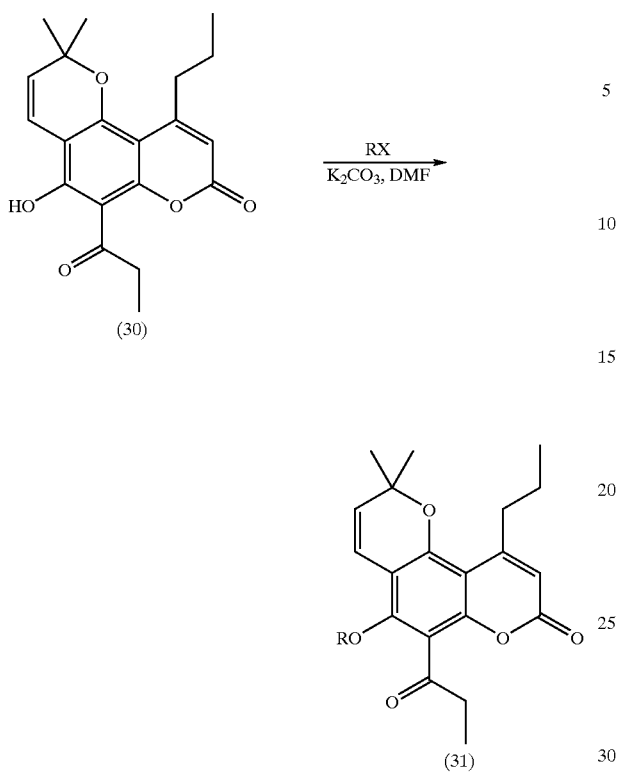

(30)

(31)

To a mixture of 5-hydroxy-2,2-dimethyl-6-propionyl-10-propyl-2H-pyrano[2,3-f]chromen-8-one (30) (1.0 eq) and potassium carbonate (5–10 eq) in DMF (10–30 mL/mmol) was added an alkylating reagent. The mixture was stirred at ambient temperature until the reaction was completed (16 to 24 h). The mixture was partitioned between water (10 volumes of DMF) and ethyl acetate (50 mL/mmol). The organic layer was separated, washed successively with water and brine, dried over anhydrous sodium sulfate and concentrated. The desired product was purified on a silica gel column chromatography eluted with 10–30% ethyl acetate in hexanes. Compound 31b is the representative and its analytical data is shown below.

5-Methoxy-2,2-dimethyl-6-propionyl-10-propyl-2H-pyrano[2,3-f]chromen-8-one (31b): 73% yield. $^1$H NMR (CDCl$_3$): 1.04 (t, J=7.5 Hz, 3H), 1.20 (t, J=7.5 Hz, 3H), 1.52 (s, 6H), 1.65 (m, 2H), 2.91 (m, 4H), 3.79 (s, 3H), 5.66 (d, J=10.0 Hz, 1H), 6.01 (s, 1H), 6.54 (J=10.0 Hz, 1H); $^{13}$C NMR (CDCl$_3$): 7.86, 13.78, 23.03, 27.76, 38.41, 38.48, 63.64, 78.15, 106.33, 111.12, 112.70, 116.39, 117.66, 128.70, 151.90, 152.59, 155.19, 157.32, 159.50, 202.88; IR: 1728, 1701 cm$^{-1}$; MS (ACPI+): 357 (M+1); Anal. Calcd. for C$_{21}$H$_{24}$O$_5$: C 70.77, H 6.79; Found: C 70.41, H 6.75.

Example 2
5-(2-Hydroxy-ethoxy)-2,2-dimethyl-6-propionyl-10-propyl-2H-pyrano[2,3-f]chromen-8-one (31e)

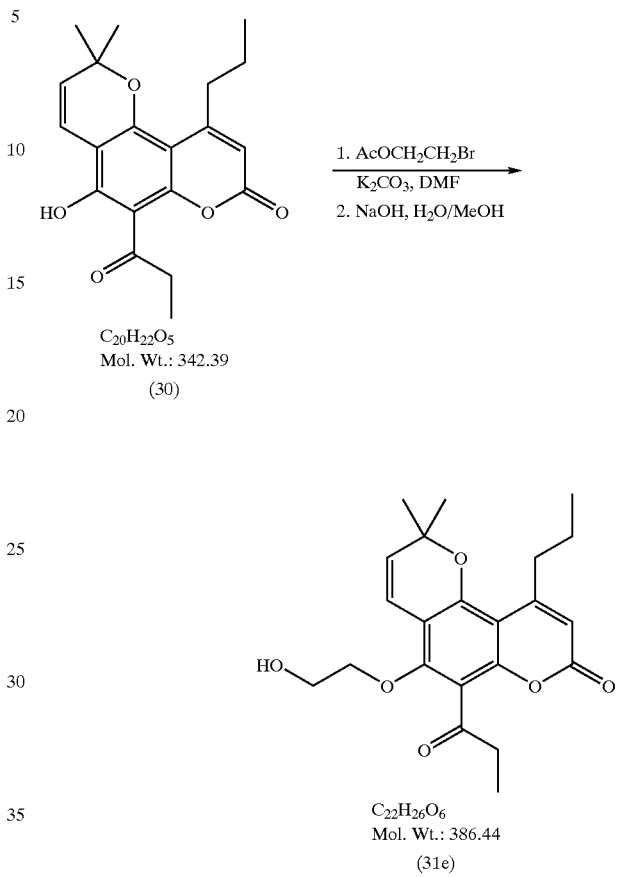

C$_{20}$H$_{22}$O$_5$
Mol. Wt.: 342.39
(30)

C$_{22}$H$_{26}$O$_6$
Mol. Wt.: 386.44
(31e)

To a solution of 5-hydroxy-2,2-dimethyl-6-propionyl-10-propyl-2H-pyrano[2,3-f]chromen-8-one (30) (3.40 g, 10 mmol, 1.0 eq) in DMF (60 mL) was added potassium carbonate (13.8 g 100 mmol, 10.0 eq) followed by 2-bromoethyl acetate (5 g, 30 mmol, 3.0 eq). The reaction mixture was stirred for 2 days at ambient temperature, which was partitioned between water (600 mL) and ethyl acetate (300 ml). The organic layer was washed with an additional portion of water (600 mL), dried and concentrated. The solid residue was re-dissolved in methanol (200 mL) followed by addition of 2 N aqueous sodium hydroxide (20 mL). The mixture was stirred for 2 h at room temperature, pH adjusted to 6.0 with concentrated hydrochloric acid and concentrated under vacuum. The residue was partitioned between water (200 mL) and ethyl acetate (200 mL). The organic layer was separated, washed successively with water (100 mL) and brine (100 mL), dried over anhydrous sodium sulfate and concentrated under vacuum. The solid residue was crystallized from cyclohexane/ethanol 80/20 and re-crystallized from methanol/water 95/5, affording 1.23 g of 31e (32% yield). $^1$H NMR (CDCl$_3$): 1.05 (t, J=7.5 Hz, 3H), 1.21 (t, J=7.5 Hz, 3H), 1.52 (s, 6H), 1.67 (m, 2H), 2.92 (m, 4H), 3.29 (t, J=6.5 Hz, 1H), 3.81 (m, 2H), 4.13 (m, 2H), 5.66 (d, J=10.0 Hz, 1H), 6.03 (s, 1H), 6.54 (J=10.0 Hz, 1H); $^{13}$C NMR (CDCl$_3$): 7.99, 13.89, 23.04, 27.60, 38.50, 38.54, 62.01, 78.08, 78.41, 106.17, 110.77, 112.63, 116.92, 117.04, 128.47, 152.27, 153.12, 154.78, 157.39, 159.38, 203.60; IR: 1708 cm$^{-1}$; MS (ACPI+): 387 (M+1); Anal. Calcd. for C$_{22}$H$_{26}$O$_6$: C 68.38, H 6.78; Found: C 68.21, H 6.90.

Example 3

5-Alkyloxy-6-(1-hydroxypropyl)-2,2-dimethyl-10-propyl-2H-pyrano[2,3-f]chromen-8-one (11)

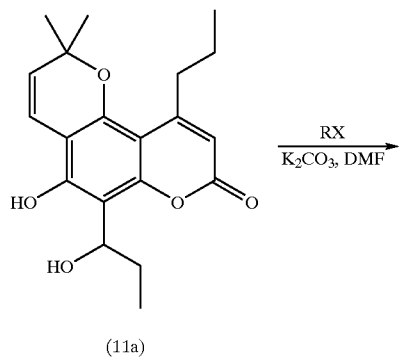

(11a)

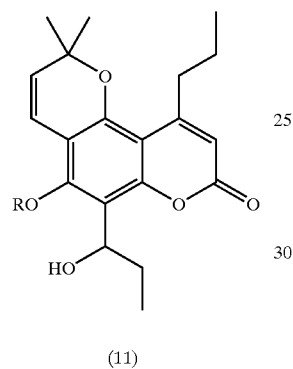

(11)

To a mixture of 5-hydroxy-6-(1-hydroxy-propyl)-2,2-dimethyl-10-propyl-2H-pyrano[2,3-f]chromen-8-one (11a) (1.0 eq) and potassium carbonate (10 eq) in anhydrous DMF (10–15 mL/mmol of starting material) was added alkylating reagent (2.0–2.5 eq). The reaction mixture was stirred overnight at ambient temperature. The mixture was poured into water (10 volumes of DMF) and extracted with ethyl acetate (50 mL/mmol of starting material). The organic layer was separated, washed with brine and dried over anhydrous sodium sulfate. Solvent was removed under vacuum and the product purified on a silica gel column eluted with 10–30% ethyl acetate in hexanes. Compound 11b is the representative and its analytical data is shown below.

6-(1-Hydroxypropyl)-5-methoxy-2,2-dimethyl-10-propyl-2H-pyrano[2,3-f]chromen-8-one (11b): 81% yield. $^1$H NMR (CDCl$_3$): 1.02 (m, 6H), 1.49 (s, 3H), 1.52 (s, 3H), 1.66 (m, 2H), 1.88 (m, 2H), 2.08 (m, 1H), 2.91 (m, 2H), 3.11 (d, J=10.0 Hz, 1H), 3.84 (s, 3H), 5.04 (m, 1H), 5.65 (d, J=10.0 Hz, 1H), 6.03 (s, 1H), 6.54 (d, J=10.0 Hz, 1H); $^{13}$C NMR (CDCl$_3$): 10.93, 13.94, 23.12, 27.32, 27.81, 30.61, 38.69, 63.05, 69.37, 77.47, 106.93, 111.01, 112.24, 117.07, 117.19, 128.49, 151.20, 153.37, 156.65, 158.14, 159.94; IR: 1729 cm$^{-1}$; MS (ACPI+): 359 (M+1), 341 (M+1-H2O); Anal. Calcd. for C$_{21}$H$_{26}$O$_5$: C 70.37, H 7.31; Found: C 70.15, H 7.35.

Example 4

5-Hydroxy-6-(1-hydroxypropyl)-2,2-dimethyl-10-propyl-2H-pyrano[2,3-f]chromen-8-one (11a)

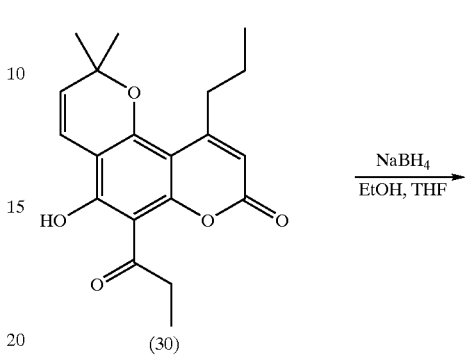

(30)

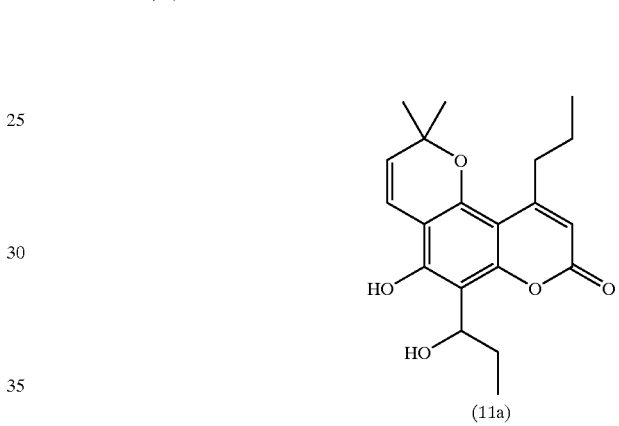

(11a)

A solution of 5-hydroxy-2,2-dimethyl-6-propionyl-10-propyl-2H-pyrano[2,3-f]chromen-8-one (30) (10.0 g, 29.2 mmol, 1.0 eq) in a mixture of ethanol (500 mL) and THF (200 mL) was cooled to 0° C. and sodium borohydride (1.7 g, 45.0 mmol, 1.54 eq) was add portionwise within 1 h. The reaction mixture was allowed to warm up room temperature and stirred for 3.5 h. The reaction was quenched with saturated aqueous ammonium chloride (20 mL). The solvents were removed under vacuum and the residue was partitioned between ice-cold 1N hydrochloric acid (200 mL) and ethyl acetate (500 mL). The organic layer was separated and washed successively with saturated sodium bicarbonate (200 mL) and brine (200 mL). The organic solution was dried over anhydrous sodium sulfate and concentrated under vacuum. The product was purified on a silica column eluted with 20–50% ethyl acetate in hexanes, affording 7.1 g of 11a (71% yield). $^1$H NMR (CDCl$_3$): 1.01 (q, J=7.5 Hz, 6H), 1.46 (s, 3H), 1.50 (s, 3H), 1.61 (m, 2H), 1.88 (m, 2H), 2.78 (m, 1H), 2.89 (m, 1H), 4.96 (d, J=3.5 Hz, 1H), 5.54 (d, J=10.0 Hz, m, 2H), 5.78 (s, 1H), 6.69 (d, J=10.0 Hz, 1H), 10.18 (s, 1H); $^{13}$C NMR (CDCl$_3$): 9.57, 14.04, 23.10, 27.47, 28.08, 29.78, 38.59, 70.73, 77.58, 102.85, 107.15, 107.62, 109.12, 116.54, 126.76, 150.89, 151.28, 156.08, 159.70, 162.01; IR: 1683 cm$^{-1}$; MS (ACPI+): 345 (M+1); Anal. Calcd. for C$_{20}$H$_{24}$O$_5$: C 69.75, H 7.02; Found: C 69.90, H 7.05.

Example 5

5-Alkyloxy-6-(1-hydroxy-propyl)-2,2-dimethyl-10-propyl-2H-pyrano[2,3-f]chromen-8-one (11)

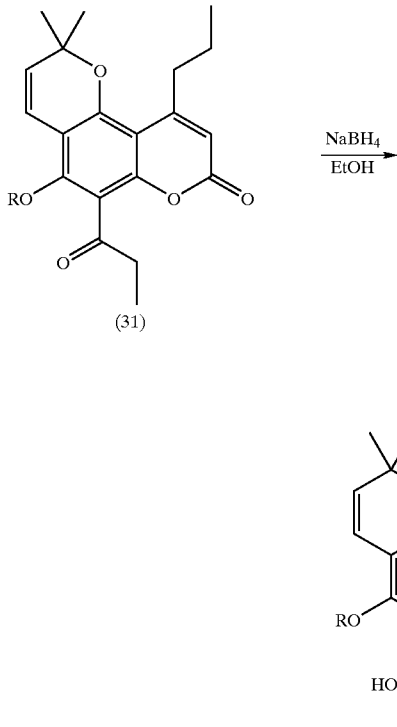

To a solution of 5-alkyloxy-2,2-dimethyl-6-propionyl-10-propyl-2H-pyrano[2,3-f]chromen-8-one (31) in ethanol (100 mL/mmol) was added portionwise sodium borohydride (3–5 eq) at 0° C. The reaction mixture was allowed to reach room temperature and was stirred until all starting material was consumed (3–4 h). Excess of sodium borohydride was quenched with saturated aqueous ammonium chloride and the mixture was concentrated under vacuum. The residue was partitioned between water and ethyl acetate. The organic layer was separated, washed successively with water and brine, dried over anhydrous sodium sulfate and concentrated under vacuum. The residue was chromatographed on silica gel to provide the desired compound 11. Compound 11e is the representative and its analytical data is shown below.

5-(2-Hydroxyethoxy)-6-(1-hydroxypropyl)-2,2-dimethyl-10-propyl-2H-pyrano[2,3-f]chromen-8-one (11e): 64% yield. $^1$H NMR (CDCl$_3$): 0.96 (t, J=7.5 Hz, 3H), 1.04 (t, J=7.5 Hz, 3H), 1.49 (s, 3H), 1.52 (s, 3H), 1.66 (m, 2H), 1.93 (m, 1H), 2.14 (m, 1H), 2.91 (m, 2H), 3.78 (br. s, 2H), 3.94 (m, 2H), 4.10 (m, 2H), 5.63 (d, J=10.0 Hz, 1H), 6.03 (s, 1H), 6.56 (d, J=10.0 Hz, 1H); $^{13}$C NMR (CDCl$_3$): 10.88, 13.93, 23.13, 27.21, 27.68, 29.82, 38.68, 61.66, 68.70, 77.00, 77.25, 106.65, 111.20, 112.134, 116.96, 117.47, 128.25, 151.31, 153.17, 156.36, 158.27, 160.36; IR: 1730 cm$^{-1}$; MS (ACPI+): 371 (M-H$_2$O+1); Anal. Calcd. for C$_{22}$H$_{28}$O$_6$: C 68.02, H 7.27; Found: C 68.04, H 7.21.

Example 6

5-Hydroxy-6-(1-hydroxypropyl)-2,2-dimethyl-10-propyl-3,4-dihydro-2H-pyrano[2,3-f]chromen-8-one (12a)

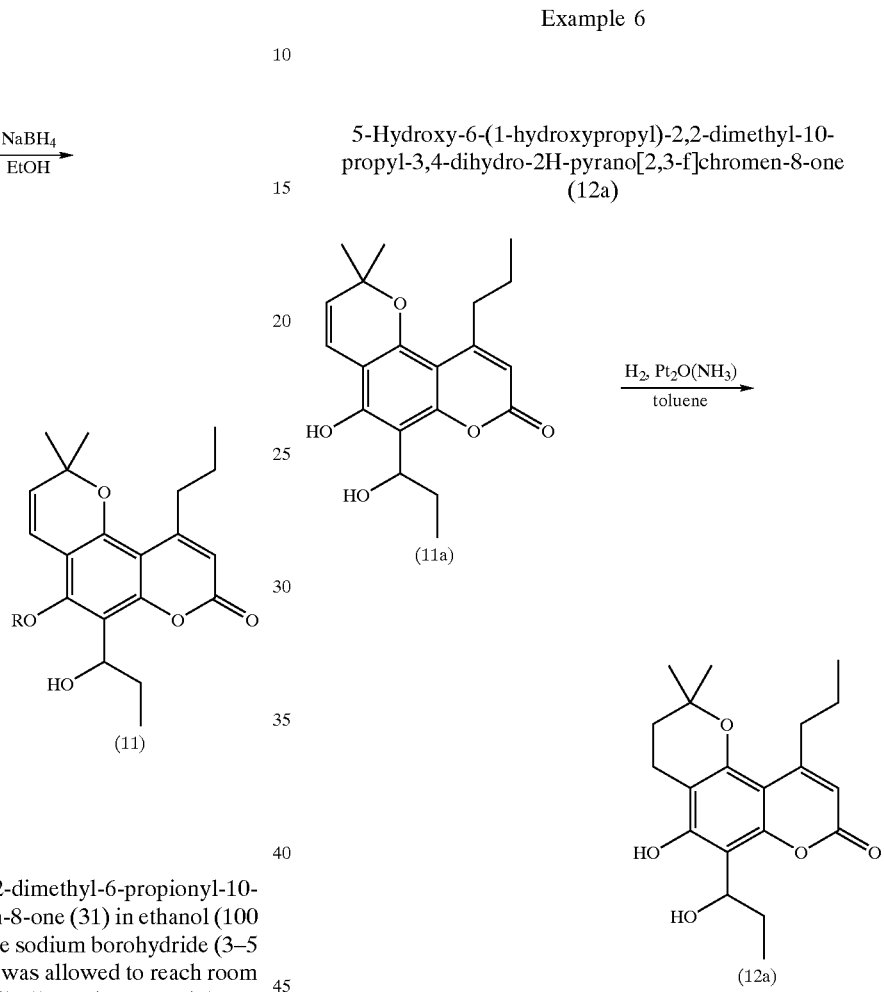

A mixture of 5-hydroxy-6-(1-hydroxypropyl)-2,2-dimethyl-10-propyl-2H-pyrano[2,3-f]chromen-8-one (11a) (400 mg, 1.16 mmol) and platinum oxide poisoned with ammonia (100 mg) in toluene (50 mL) was hydrogenated under atmospheric pressure of hydrogen at ambient temperature for 2 hours. Column chromatography on silica gel eluted with 30% ethyl acetate in hexanes and subsequent crystallization from 20% acetone in hexanes provided 252 mg of 12a (63% yield). $^1$H NMR (CDCl$_3$): 1.02 (t, J=7.5 Hz, 3H), 1.22 (t, J=7.5 Hz, 3H), 1.41 (s, 6H), 1.62 (m, 2H), 1.82 (t, J=6.5 Hz, 2H), 2.75 (t, J=6.5 Hz, 2H), 2.91 (m, 4H), 3.78 (s, 3H), 6.01 (s, 1H); $^{13}$C NMR (CDCl$_3$): 7.97, 13.84, 17.20, 23.19, 26.66, 31.33, 38.48, 38.99, 62.14, 76.35, 106.14, 110.66, 112.48, 116.55, 151.24, 153.50, 157.51, 157.92, 159.92, 203.40; IR: 1724, 1704 cm$^{-1}$; MS (ACPI+): 359 (M+1); Anal. Calcd. for C$_{21}$H$_{26}$O$_5$: C 70.37, H 7.31; Found: C 70.15, H 7.28.

Example 7

5-Alkyloxy-6-(1-hydroxy-propyl)-2,2-dimethyl-10-propyl-3,4-dihydro-2H-pyrano[2,3-f]chromen-8-one (12)

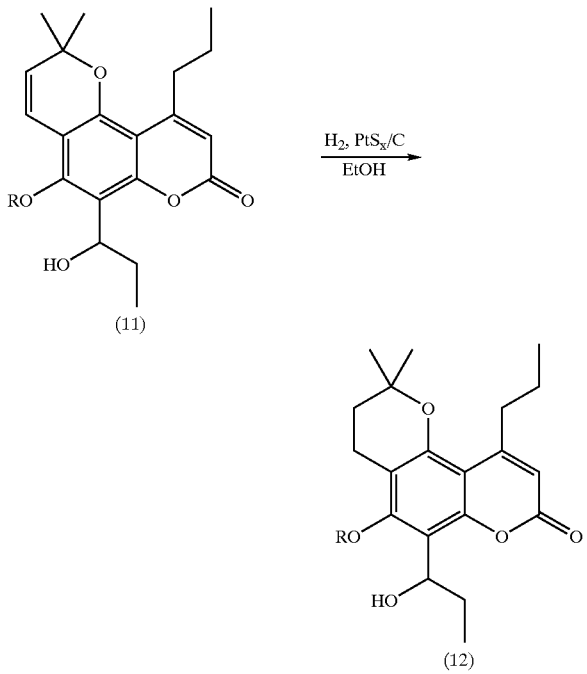

A solution of 5-alkyloxy-6-(1-hydroxy-propyl)-2,2-dimethyl-10-propyl-2H-pyrano[2,3-f]chromen-8-one (11) in ethanol (50 mL/mmol) was flushed with nitrogen for 15 min. Sulfided platinum on carbon (Aldrich, 100–150 mg per 1 mmol) was added to the solution and the mixture stirred overnight at ambient temperature under atmospheric pressure of hydrogen. The mixture was filtered through a pad of Celite and the filtrate was concentrated under vacuum. The product was purified on a silica column eluted with 15–30% ethyl acetate in hexanes. The representative compounds are shown below.

6-(1-Hydroxypropyl)-5-methoxy-2,2-dimethyl-10-propyl-3,4-dihydro-2H-pyrano[2,3-f]chromen-8-one (12b): 73% yield. $^1$H NMR (CDCl$_3$): 1.02 (m, 6H), 1.38 (s, 3H), 1.42 (s, 3H), 1.62 (m, 2H), 1.85 (m, 4H), 2.13 (m, 1H), 2.83 (m, 4H), 3.08 (d, J=11.0 Hz, 1H), 3.83 (s, 3H), 5.01 (m, 1H), 6.01 (s, 1H); $^{13}$C NMR (CDCl$_3$): 11.06, 13.90, 17.50, 23.27, 26.11, 27.28, 30.64, 31.52, 39.23, 61.48, 69.63, 75.79, 106.98, 110.57, 112.11, 116.38, 152.08, 152.81, 156.71, 158.81, 160.25; IR: 1711 cm$^{-1}$; MS (ACPI+): 361 (M+1), 343 (M+1-H2O); Anal calc for C$_{21}$H$_{28}$O$_5$·1/3H$_2$O: C 68.83, H 7.88; Found: C 68.50, H 7.89.

5-(2-Hydroxyethoxy)-6-(1-hydroxypropyl)-2,2-dimethyl-10-propyl-3,4-dihydro-2H-pyrano[2,3-f]chromen-8-one (12e): 365 yield. $^1$H NMR (CDCl$_3$): 0.94 (t, J=7.0 Hz, 3H), 1.03 (t, J=7.0 Hz, 3H), 1.40 (s, 3H), 1.41 (s, 3H), 1.64 (m, 2H), 1.86 (m, 3H), 2.17 (m, 1H), 2.80 (t, J=6.5 Hz, 2H), 2.90 (m, 2H), 3.92 (m, 1H), 4.01 (m, 1H), 4.14 (m, 1H), 5.17 (t, J=7.0 Hz, 1H); $^{13}$C NMR (CDCl$_3$): 11.02, 13.90, 17.98, 23.27, 26.40, 27.01, 29.89, 31.54, 39.24, 61.94, 69.07, 75.11, 75.78, 106.76, 110.68, 112.04, 116.18, 152.13, 152.58, 158.18, 158.79, 160.56; IR: 1721, 1685 cm$^{-1}$; MS (ACPI+): 373 (M+1-H2O); Anal calc for C$_{22}$H$_{30}$O$_6$: C 67.67, H 7.74; Found C 67.31, H 7.69.

Example 8

5,10-Dihydroxy-8,9-dimethyl-4-propyl-9,10-dihydro-8H-pyrano[2,3-f]chromen-2-one (cis- and trans-17a)

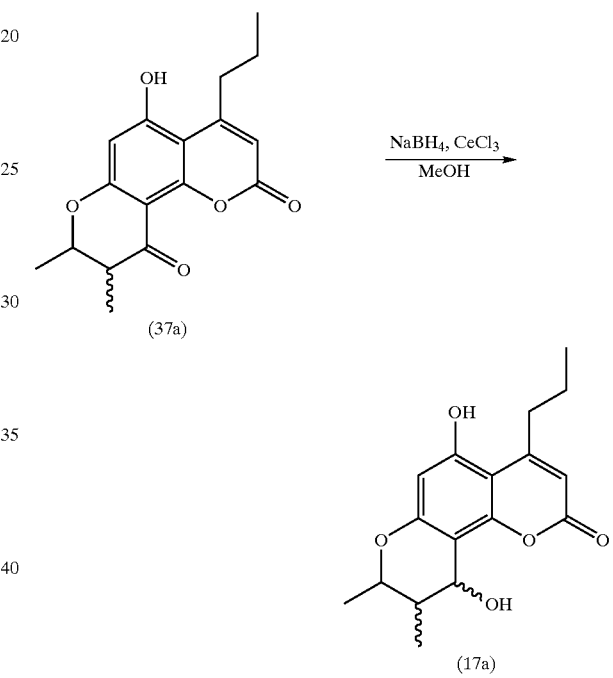

A solution of 5-hydroxy-8,9-dimethyl-4-propyl-8,9-dihydro-pyrano[2,3-f]chromene-2,10-dione (a mixture of cis- and trans-37a) (2 g, 6.61 mmol, 1.00 eq) and cerium(III) chloride septahydrate (2.5 g, 6.71 mol, 1.02 eq) in methanol (300 mL) was cooled to 0° C. Sodium borohydride (0.62 g, 16.39 mmol, 2.48 eq) was added portionwise to the stirred solution within 1 h while the temp was maintained at 0–5° C. The reaction mixture was allowed to warm up to room temperature and stirring continued for 2 h. Solvent was removed under vacuum and the residue partitioned between dichloromethane (200 mL) and ice-cold 1N hydrochloric acid (100 mL). The organic layer was separated, washed successively with saturated solution of sodium bicarbonate (200 mL) and brine (200 mL). The organic layer was dried over anhydrous sodium sulfate and concentrated under vacuum yielding 1.97 g (98%) of a mixture of cis- and trans-17a. The crude product was used for the next step without further purification.

Example 9

5-Alkyloxy-10-hydroxy-8,9-dimethyl-4-propyl-9,10-dihydro-8H-pyrano[2,3-f]chromen-2-one (cis- and trans-17)

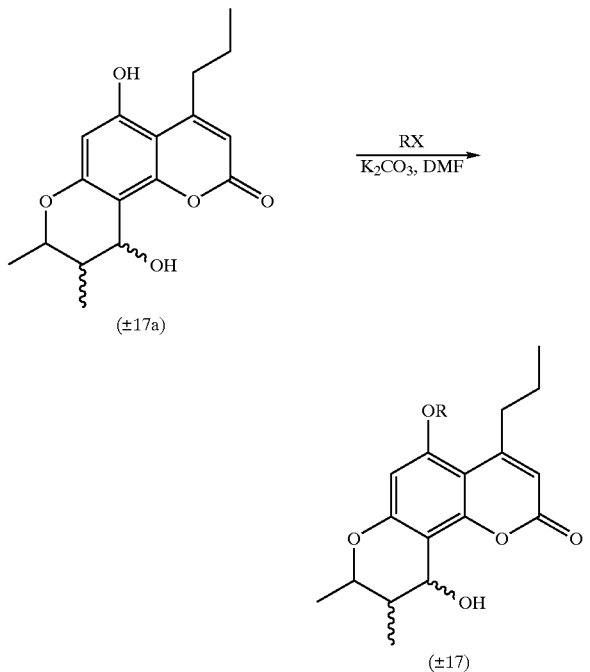

To a stirred mixture of a crude 10-hydroxy-5-methoxy-8,9-dimethyl-4-propyl-9,10-dihydro-8H-pyrano[2,3-f]chromen-2-one (a mixture of cis- and trans-17a) (0.5 g, 1.64 mmol, 1.00 eq) and potassium carbonate (4.18 g, 30.24 mmol, 18.44 eq) in anhydrous DMF (50 mL) was added alkylating reagent (4.00–5.00 eq). The reaction mixture was stirred overnight at room temperature. The mixture was then poured into water (200 mL) and extracted with ethyl acetate (100 mL). The organic layer was separated and washed successively with water (2×100 mL) and brine. The organic solution was dried over anhydrous sodium sulfate and concentrated under vacuum. The residue was purified on short silica column (15–30% ethyl acetate in hexanes) to provide a mixture of isomers. Two major isomers were separated on preparative HPLC (Alltech Econosil 10 um, 250×22 mm column, 15–30% ethyl acetate in hexanes) in a ratio of 65:45. The representative compounds are shown below.

5-Methoxy-10-hydroxy-8,9-dimethyl-4-propyl-9,10-dihydro-8H-pyrano[2,3-f]chromen-2-one (cis- and trans-17b): 69% combined yield. 8,9-trans-17b: $^1$H NMR (500 MHz, CDCl$_3$) δ 1.01 (3H, t, J=7.5 Hz), 1.15 (3H, d, J=7.0 Hz), 1.42 (3H, d, J=6.5 Hz), 1.61 (2H, sextet, J=7.0 Hz), 2.29 (1H, ddq, J=3.5, 4.5, 7.5 Hz), 2.80–2.92 (2H, m), 3.17 (1H, d, J=3.5 Hz), 3.86 (3H, s), 4.37 (1H, dq, J=3.3, 6.6 Hz), 5.10 (1H, dd, J=3.5, 5.0 Hz), 5.96 (1H, s), 6.25 (1H, s); $^{13}$C NMR (125.65 Hz, CDCl$_3$) δ 9.5, 14.0, 16.1, 22.8, 35.7, 38.7, 55.7, 75.7, 96.0, 104.1, 106.0, 109.9, 155.6, 156.9, 158.1, 159.0, 160.7; IR (film) 3471, 2998, 2963, 2937, 2891, 2873, 1702, 1614, 1584, 1486, 1455, 1378, 1346, 1300, 1280, 1204, 1158, 1115, 1063, 1031, 965, 820 cm$^{-1}$; MS (APCI) m/e 319 (M+1), 301 (M-OH); Anal. Calcd. for C$_{18}$H$_{22}$O$_5$: C, 67.91; H, 6.97. Found: C, 67.65; H, 7.08. 8,9-cis-17b: $^1$H NMR (500 MHz, CDCl$_3$) δ 1.01 (3H, t, J=7.5 Hz), 1.14 (3H, d, J=7.0 Hz), 1.45 (3H, d, J=6.0 Hz), 1.61 (2H, sextet, J=7.3 Hz), 1.94 (1H, sextet, J=7.2 Hz), 2.80–2.92 (2H, m), 3.60 (1H, d, J=2.5 Hz), 3.85 (3H, s), 3.95 (1H, dq, J=8.7, 6.2 Hz), 4.73 (1H, dd, J=2.5, 7.5 Hz), 5.96 (1H, s), 6.26 (1H, s); $^{13}$C NMR (125.65 Hz, CDCl$_3$) δ 14.0, 15.1, 18.9, 22.9, 38.7, 40.4, 55.8, 66.9, 77.1, 95.9, 104.4, 106.5, 109.9, 155.5, 157.9, 158.0, 159.0, 160.5; IR (film) 3480, 3403, 2965, 2934, 2898, 2872, 1695, 1615, 1585, 1465, 1374, 1346, 1327, 1297, 1233, 1200, 1166, 1129, 1116, 1109, 1060, 1031, 819 cm$^{-1}$; MS (APCI) m/e 319 (M+1), 301 (M-OH); Anal. Calcd. for C$_{18}$H$_{22}$O$_5$.1/4H$_2$O: C, 66.96; H, 7.02. Found: C, 66.92; H, 7.13.

5-(i-Propyloxy)-10-hydroxy-8,9-dimethyl-4-propyl-9,10-dihydro-8H-pyrano[2,3-f]chromen-2-one (cis- and trans-17e): 74% combined yield. 8,9-trans-17e: $^1$H NMR (500 MHz, CDCl$_3$) δ 1.01 (3H, t, J=7.2 Hz), 1.14 (3H, d, J=7.5 Hz), 1.40 (6H, d, J=6.0 Hz), 1.41 (3H, d, J=6.5 Hz), 1.63 (2H, d-sextet, J=2.2, 7.9 Hz), 2.24–2.32 (1H, m), 2.82–2.95 (2H, m), 3.31 (1H, br. s), 4.35 (1H, dq, J=3.1, 6.7 Hz), 4.64 (1H, septet, J=6.0 Hz), 5.09 (1H, d, J=5.0 Hz), 5.94 (1H, s), 6.22 (1H, s); $^{13}$C NMR (125.65 Hz, CDCl$_3$) δ 9.5, 13.9, 16.1, 21.7, 23.2, 35.8, 39.0, 62.9, 70.7, 75.7, 97.0, 104.5, 105.5, 109.9, 155.8, 156.2, 156.9, 159.3, 160.8; IR (film) 3433, 2975, 2934, 2874, 1723, 1701, 1615, 1584, 1480, 1451, 1381, 1349, 1331, 1298, 1231, 1202, 1161, 1130, 1108, 1062, 1034, 967, 830 cm$^{-1}$; MS(APCI) m/e 347 (M+1); Anal. Calcd. for C$_{20}$H$_{26}$O$_5$. 2/3 H$_2$O: C, 67.02; H, 7.69. Found: C, 67.08; H, 7.68. 8,9-cis-17e: $^1$H NMR (500 MHz, CDCl$_3$) δ 1.01 (3H, t, J=7.5 Hz), 1.14 (3H, d, J=7.0 Hz), 1.39 (3H, d, J=6.5 Hz), 1.41 (3H, d, J=6.0 Hz), 1.44 (3H, d, J=6.5 Hz), 1.62 (2H, sextet, J=7.3 Hz), 1.91–1.97 (1H, m), 2.83–2.94 (2H, m), 3.61 (1H, br. s), 3.90–3.98 (1H, m), 4.63 (1H, septet, J=6.0 Hz), 4.72 (1H, d, J=8.0 Hz), 5.94 (1H, s), 6.23 (1H, s); $^{13}$C NMR (125.65 Hz, CDCl$_3$) δ 13.9, 15.1, 18.9, 21.6, 21.8, 23.2, 39.0, 40.5, 67.0, 70.7, 76.7, 96.9, 104.8, 106.1, 109.9, 155.7, 156.1, 157.9, 159.3, 160.6; IR (film) 3357, 2969, 2934, 2873, 1722, 1696, 1615, 1585, 1480, 1453, 1377, 1350, 1295, 1232, 1199, 1169, 1110, 1063, 1029 cm$^{-1}$; MS (APCI) m/e 347 (M+1), 329 (M-OH); Anal. Calcd. for C$_{20}$H$_{26}$O$_5$.H$_2$O: C, 65.92; H, 7.74. Found: C, 65.46; H, 7.48.

5-(Prop-2-ynyloxy)-10-hydroxy-8,9-dimethyl-4-propyl-9,10-dihydro-8H-pyrano[2,3-f]chromen-2-one (cis- and trans-17f): 71% combined yield. 8,9-trans-17f: $^1$H NMR (500 MHz, CDCl$_3$) δ 1.03 (3H, t, J=7.2 Hz), 1.15 (3H, d, J=7.0 Hz), 1.42 (3H, d, J=7.0 Hz), 1.63 (2H, sextet, J=7.1 Hz), 2.28 (1H, ddq, J=3.0, 5.0, 7.0 Hz), 2.58 (1H, t, J=2.5 Hz), 2.82–2.94 (2H, m), 3.21 (1H, d, J=3.0 Hz), 4.37 (1H, dq, J=3.0, 6.7 Hz), 4.72 and 4.73 (2H, d-AB type, J$_d$=2.5 Hz, J$_{AB}$=15.4 Hz), 5.10 (1H, dd, J=2.0, 5.0 Hz), 5.98 (1H, s), 6.32 (1H, s); $^{13}$C NMR (125.65 Hz, CDCl$_3$) δ 9.5, 13.9, 16.1, 23.0, 35.7, 38.8, 56.4, 62.9, 75.8, 76.4, 97.2, 104.3, 106.7, 107.9, 110.4, 155.6, 155.9, 156.7, 158.7, 160.5; IR (film) 3431, 3288, 2962, 2936, 2874, 2125, 1706, 1616, 1588, 1483, 1454, 1384, 1349, 1297, 1231, 1202, 1161, 1130, 1107, 1064, 1035, 1000, 968 cm$^{-1}$; MS (APCI) m/e 343 (M+1), 325 (M-OH); Anal. Calcd. for C$_{20}$H$_{22}$O$_5$. 1/2H$_2$O: C, 68.36; H, 6.60. Found: C, 68.26; H, 6.57. 8,9-cis-17f: $^1$H NMR (500 MHz, CDCl$_3$) δ 1.03 (3H, t, J=7.2 Hz), 1.15 (3H, d, J=7.0 Hz), 1.45 (3H, d, J=6.5 Hz), 1.63

(2H, sextet, J=7.2 Hz), 1.94 (1H, sextet, J=7.8 Hz), 2.58 (1H, t, J=2.5 Hz), 2.82–2.94 (2H, m), 3.70 (1H, d, J=3.0 Hz), 3.95 (1H, dq, J=8.7, 6.7 Hz), 4.72 (3H, m), 5.99 (1H, s), 6.32 (1H, s); $^{13}$C NMR (125.65 Hz, CDCl$_3$) δ 13.9, 15.1, 18.9, 23.0, 38.8, 40.4, 56.4, 66.9, 76.4, 76.8, 97.0, 104.6, 107.4, 107.9, 110.3, 155.5, 155.7, 157.8, 158.9, 160.5; IR (film) 3467, 3380, 3212, 2964, 2933, 2899, 2872, 2117, 1699, 1613, 1589, 1458, 1384, 1344, 1326, 1292, 1259, 1235, 1170, 1127, 1110, 1065, 1034, 997, 813 cm$^{-1}$; MS (APCI) m/e 343 (M+1), 325 (M-OH); Anal. Calcd. for C$_{20}$H$_{22}$O$_5$.1/2H$_2$O: C, 68.36; H, 6.60. Found: C, 68.37; H, 6.91.

5-(Allyloxy)-10-hydroxy-8,9-dimethyl-4-propyl-9,10-dihydro-8H-pyrano[2,3-f]chromen-2-one (cis- and trans-17c): 69% combined yield. 8,9-trans-17c: $^1$H NMR (500 MHz, CDCl$_3$) δ 0.99 (3H, t, J=7.2 Hz), 1.14 (3H, d, J=7.0 Hz), 1.41 (3H, d, J=6.5 Hz), 1.61 (2H, sextet, J=7.5 Hz), 2.24–2.31 (1H, m), 2.82–2.94 (2H, m), 3.29 (1H, br. s), 4.36 (1H, dq, J=3.5, 6.7 Hz), 4.56 (2H, d, J=6.0 Hz), 5.09 (1H, d, J=5.0 Hz), 5.36 (1H, dd, J=2.0, 9.5 Hz), 5.43 (1H, dd, J=1.5, 17.0 Hz), 5.96 (1H, s), 6.03–6.11 (1H, m), 6.24 (1H, s); $^{13}$C NMR (125.65 Hz, CDCl$_3$) δ 9.7, 13.9, 16.1, 23.0, 35.7, 38.8, 62.9, 70.0, 75.7, 96.9, 104.2, 106.1, 110.0, 119.2, 132.0, 155.6, 156.8, 157.1, 159.0, 160.7; IR (film) 3436, 3083, 2964, 2934, 2874, 1723, 1617, 1587, 1483, 1456, 1423, 1382, 1350, 1299, 1231, 1195, 1162, 1108, 1064, 1034, 991, 967, 924, 819 cm$^{-1}$; MS (APCI) m/e 345 (M+1); Anal. Calcd. for C$_{20}$H$_{24}$O$_5$: C, 69.75; H, 7.02. Found: C, 69.17; H, 7.09. 8,9-cis-17c: $^1$H NMR (500 MHz, CDCl$_3$) δ 0.99 (3H, t, J=7.2 Hz), 1.14 (3H, d, J=7.0 Hz), 1.45 (3H, d, J=6.0 Hz), 1.61 (2H, sextet, J=7.3 Hz), 1.94 (1H, sextet, J=7.0 Hz), 2.82–2.94 (2H, m), 3.67 (1H, d J=3.0 Hz), 3.94 (1H, dq, J=8.5, 6.2 Hz), 4.56 (2H, d, J=5.5 Hz), 4.72 (1H, dd, J=2.5, 8.0 Hz), 5.36 (1H, dd, J=1.0, 10.5 Hz), 5.42 (1H, dd, J=1.0, 17.0 Hz), 5.96 (1H, s), 6.03–6.11 (1H, m), 6.25 (1H, s); $^{13}$C NMR (125.65 Hz, CDCl$_3$) δ 13.9, 15.1, 18.9, 23.0, 38.9, 40.4, 66.9, 70.0, 76.7, 96.8, 104.5, 106.7, 110.0, 119.2, 132.0, 155.5, 156.9, 157.8, 159.1, 160.5; IR (film) 3448, 2970, 2936, 2891, 2870, 1690, 1615, 1583, 1485, 1455, 1377, 1359, 1347, 1289, 1229, 1200, 1175, 1106, 1065, 1054, 1036, 819 cm$^{-1}$; MS (APCI) m/e 345 (M+1), 327 (M-OH); Anal. Calcd. for C$_{20}$H$_{24}$O$_5$: C, 69.75; H, 7.02. Found: C, 68.94; H, 7.16

5-(1-Methylallyloxy)-10-hydroxy-8,9-dimethyl-4-propyl-9,10-dihydro-8H-pyrano[2,3-f]chromen-2-one (cis- and trans-17g): 75% combined yield. 8,9-trans-17g: $^1$H NMR (500 MHz, CDCl$_3$) δ 1.01 (3H, t, J=7.2 Hz) [0.98 (t, J=7.2 Hz)], 1.14 (3H, d, J=7.0 Hz) [1.13 (d, J=7.0 Hz)], 1.40 (3H, d, J=6.5 Hz), 1.50 (3H, d, J=6.5 Hz) [1.51 (d, J=6.0 Hz)], 1.64 (2H, sextet, J=7.2 Hz) [1.61 (sextet, J=7.1 Hz)], 2.27 (1H, ddq, J=1.0, 4.5, 7.0 Hz), 2.82–2.96 (2H, m), 3.18 (1H, br. s), 4.34 (1H, dq, J=3.0, 7.0 Hz), 4.89 (1H, sextet, J=4.0 Hz), 5.10 (1H, dd, J=2.5, 4.5 Hz), 5.25 (1H, d, J=10.5 Hz), 5.30 (1H, dd, J=1.0, 16.5 Hz), 5.86–5.95 (1H, m), 5.95 (1H, s), 6.23 (1H, s) [6.24 (1H, s)]; $^{13}$C NMR (125.65 Hz, CDCl$_3$) δ 9.5, 13.9, 16.1, 21.0 (21.2), 23.2 (23.1), 35.7, 39.0 (38.9), 63.0, 69.7, 75.7 (75.6), 98.0 (96.8), 104.4 (104.2), 105.8 (105.7), 110.1 (110.0), 116.7 (116.6), 137.8, 155.7, 156.3, 156.7 (157.2), 159.1, 160.7; IR (film) 3438, 3086, 2963, 2934, 2874, 1721, 1616, 1586, 1480, 1448, 1380, 1349, 1296, 1231, 1199, 1162, 1130, 1104, 1064, 1035, 967 cm$^{-1}$; MS (APCI) m/e 359 (M+1), 341 (M-OH), 287 (M-OH—C$_4$H$_6$); Anal. Calcd. for C$_{21}$H$_{26}$O$_5$: C, 70.37; H, 7.31. Found: C, 69.99; H, 7.21. 8,9-cis-17g: $^1$H NMR (500 MHz, CDCl$_3$) δ 1.01 (3H, t, J=7.2 Hz) [0.98 (t, J=7.2 Hz)], 1.14 (3H, d, J=6.5 Hz) [1.13 (d, J=7.0 Hz)], 1.43 (3H, d, J=6.5 Hz), 1.50 (3H, d, J=6.5 Hz) [1.51 (d, J=6.0 Hz)], 1.64 (2H, sextet, J=7.5 Hz) [1.61 (sextet, J=7.2 Hz)], 1.92 (1H, sextet, J=7.2 Hz), 2.82–2.96 (2H, m), 3.58 (1H, br. s), 3.92 (1H, m), 4.71 (1H, dd, J=2.0, 7.5 Hz), 4.88 (1H, sextet, J=6.0 Hz), 5.23–5.32 (2H, m), 5.85–5.95 (1H, m), 5.96 (1H, s), 6.24 (1H, s) [6.23 (1H, s)]; $^{13}$C NMR (125.65 Hz, CDCl$_3$) δ 13.8, 15.1, 18.9, 21.1, 23.2 (23.1), 39.0 (38.9), 40.4, 67.0, 69.7, 75.6 (75.5), 97.8 (96.6), 104.6 (104.5), 106.4, 110.0, 116.7 (116.6), 137.8 (137.6), 155.5, 156.1, 157.8 (157.1), 159.1, 160.5; IR (film) 3427, 2966, 2933, 2873, 1723, 1617, 1587, 1480, 1448, 1376, 1293, 1232, 1195, 1172, 1104, 1064, 1028, 992, 895, 830 cm$^{-1}$; MS (APCI) m/e 359 (M+1), 341 (M-OH), 287 (M-OH—C$_4$H$_6$); Anal. Calcd. for C$_{21}$H$_{26}$O$_5$.1/2H$_2$O: C, 68.65; H, 7.27. Found: C, 68.89; H, 7.39.

5-(2-Methylallyloxy)-10-hydroxy-8,9-dimethyl-4-propyl-9,10-dihydro-8H-pyrano[2,3-f]chromen-2-one (cis- and trans-17h): 75% combined yield. 8,9-trans-17h: $^1$H NMR (500 MHz, CDCl$_3$) δ 0.98 (3H, t, J=7.2 Hz), 1.14 (3H, d, J=7.0 Hz), 1.41 (3H, d, J=7.0 Hz), 1.62 (2H, sextet, J=7.2 Hz), 1.87 (3H, s), 2.24–2.31 (1H, m), 2.82–2.94 (2H, m), 3.23 (1H, d, J=3.0 Hz), 4.36 (1H, dq, J=3.2, 6.7 Hz), 4.47 (2H, s), 5.06 (1H, s), 5.09 (2H, s), 5.97 (1H, s), 6.25 (1H, s); $^{13}$C NMR (125.65 Hz, CDCl$_3$) δ 9.5, 13.8, 16.1, 22.8, 35.7, 38.7, 62.9, 73.2, 75.7, 97.0, 104.2, 106.1, 109.9, 114.5, 139.6, 155.6, 155.8, 157.4, 159.0, 160.6; IR (film) 3513, 3083, 2957, 2932, 2911, 2874, 1707, 1616, 1587, 1487, 1460, 1438, 1382, 1368, 1261, 1202, 1159, 1132, 1110, 1063, 1033, 970, 923, 843, 823 cm$^{-1}$; MS (APCI) m/e 359 (M+1), 341 (M-OH); Anal. Calcd. for C$_{21}$H$_{26}$O$_5$: C, 70.37; H, 7.31. Found: C, 70.08; H, 7.32. 8,9-cis-17h: $^1$H NMR (500 MHz, CDCl$_3$) δ 0.98 (3H, t, J=7.2 Hz), 1.14 (3H, d, J=6.5 Hz), 1.44 (3H, d, J=6.0 Hz), 1.62 (2H, sextet, J=7.3 Hz), 1.86 (3H, s), 1.94 (1H, sextet, J=7.2 Hz), 2.82–2.94 (2H, m), 3.71 (1H, br. s), 3.94 (1H, dq, J=8.7, 6.2 Hz), 4.47 (2H, s), 4.72 (1H, d, J=7.5 Hz), 5.06 (1H, s), 5.09 (1H, s), 5.97 (1H, s), 6.25 (1H, s); $^{13}$C NMR (125.65 Hz, CDCl$_3$) δ 13.8, 15.1, 18.9, 19.7, 22.8, 38.8, 40.4, 66.9, 73.2, 76.7, 96.9, 104.5, 106.7, 109.8, 114.5, 139.6, 155.5, 157.2, 157.8, 159.1, 160.6; IR (film) 3441, 3203, 2938, 2900, 2874, 1698, 1618, 1586, 1486, 1384, 1355, 1325, 1297, 1275, 1229, 1210, 1174, 1127, 1109, 1068, 1029, 882 cm$^{-1}$; MS (APCI) m/e 359 (M+1), 341 (M-OH); Anal. Calcd. for C$_{21}$H$_{26}$O$_5$.1/4 H$_2$O: C, 69.50; H, 7.36. Found: C, 69.47; H, 7.38.

Example 10

5,7-Dimethoxy-8-propionyl-4-propyl-chromen-2-one (43b)

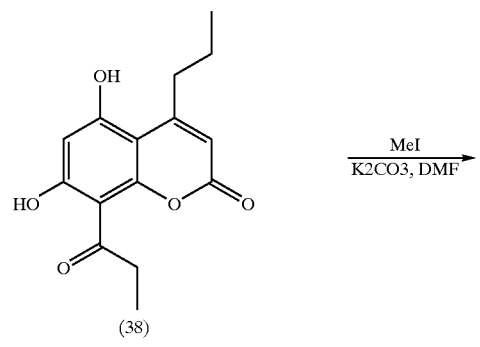

-continued

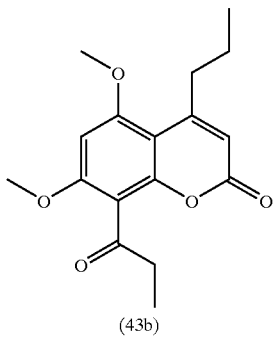

(43b)

The same procedure as used in the preparation of 31a. Compound 43b: $^1$H NMR (CDCl$_3$): 1.01 (t, 3H), 1.19 (t, 3H), 1.59 (m, 2H), 2.85 (m, 4H), 3.89 (s, 3H), 3.94 (s, 3H), 5.96 (s, 1H), 6.32 (s, 1H); Calcd. for C$_{17}$H$_{20}$O$_5$: C 67.09, H 6.62; Found C 67.21, H 6.66.

Example 11

5,7-Bis-allyloxy-8-(1-hydroxy-propyl)-4-propyl-chromen-2-one (21d)

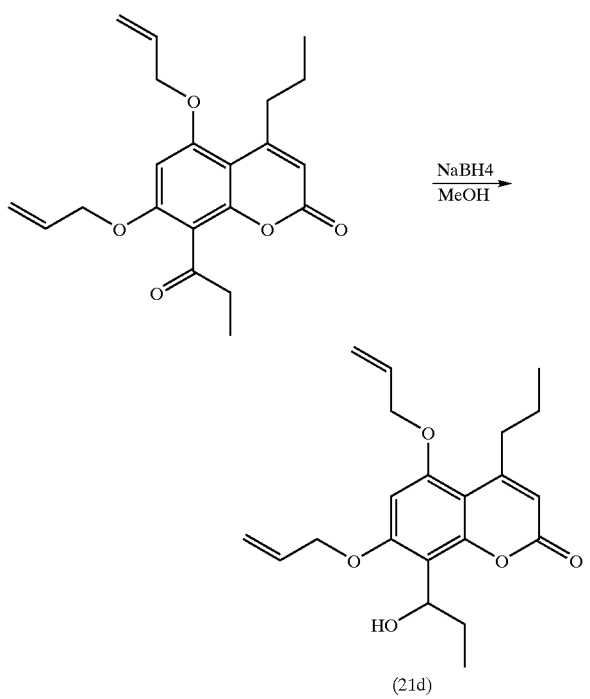

The same procedure as used in the preparation of 11e. Compound 21d: $^1$H NMR (CDCl$_3$): 0.89 (t, J=7.5 Hz, 3H), 0.90 (t, J=7.5 Hz, 3H), 1.61 (m, 2H), 1.86 (m, 1H), 2.04 (m, 1H), 2.89 (t, J=7.5 Hz, 2H), 3.28 (d, 1H), 4.62 (d, 2H), 4.66 (d, 2H), 5.40 (m, 2H), 5.99 (s, 1H), 6.06 (m, 2H), 6.37 (s, 1H); $^{13}$C NMR (CDCl$_3$): 10.63, 13.86, 22.89, 30.23, 38.82, 68.76, 69.48, 70.10, 93.62, 104.42, 111.06, 112.79, 118.56, 119.20, 132.05, 153.79, 156.52, 158.24, 158.73, 160.32; IR: 1708 cm$^{-1}$; MS (APCI+): 359 (M+1), 341 (M-H$_2$O+1).

Example 12

6-(1-Aminopropyl)-5-hydroxy-2,2-dimethyl-10-propyl-2H-pyrano[2,3-f]chromen-8-one (24a)

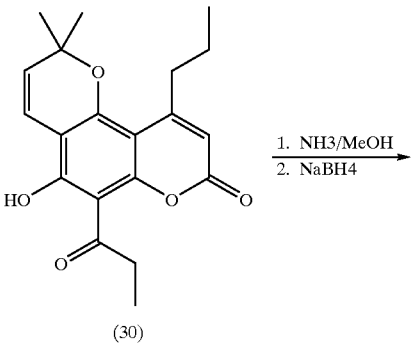

(30)

1. NH3/MeOH
2. NaBH4

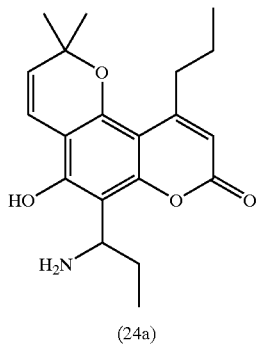

(24a)

5-Hydroxy-2,2-dimethyl-6-propionyl-10-propyl-2H-pyrano[2,3-f]chromen-8-one (30) (1.0 g, 2.9 mmol, 1.0 eq) was dissolved in 7 N ammonia in methanol (100 mL, 0.7 mol, 241 eq). The mixture was stirred overnight at ambient temperature. Solvent and excess of ammonia were removed under vacuum and the residue re-dissolved in methanol (100 mL). The solution was cooled to 0° C. and sodium borohydride (550 mg, 14.6 mmol, 5.0 eq) added portionwise. The mixture was allowed to warm up room temperature and stirred for 3 h. The mixture was then poured into ice-water and pH adjusted to 8.5 with concentrated hydrochloric acid. The product was extracted into ethyl acetate (3×50 mL). The extracts were combined and washed with brine, dried over anhydrous sodium sulfate and concentrated under vacuum. The residue was chromatographed on silica gel column eluted with 5–10% methanol in dichloromethane to yield 612 mg of 24a (61% yield). $^1$H NMR (CDCl$_3$): 0.97 (t, J=7.5 Hz, 3H), 1.03 (t, J=7.5 Hz, 3H), 1.47 (s, 3H), 1.49 (s, 3H), 1.67 (m, 2H), 1.78 (m, 2H), 2.89 (m, 2H), 4.85 (t, J=7.0 Hz, 1H), 5.52 (d, J=10.0 Hz, 1H), 5.88 (s, 1H), 6.67 (d, J=10.0 Hz, 1H); $^{13}$C NMR (DMSO-d$_6$): 10.17, 13.99, 23.54, 26.24, 27.23, 27.31, 37.99, 49.84, 76.35, 96.60, 102.88, 103.95, 107.80, 118.29, 123.55, 150.87, 153.82, 158.66, 160.26, 167.83; IR: 1683 cm$^{-1}$; MS (ACPI+): 344 (M+1), 327 (M-NH$_3$+1); Anal. Calcd. for C$_{20}$H$_{25}$NO$_4$: C 69.95, H 7.34, N 4.08; Found C 69.97, H 7.30, N 4.08.

Example 13

5-Alkyloxy-6-(1-amino-propyl)-2,2-dimethyl-10-propyl-2H-pyrano[2,3-f]chromen-8-one (24)

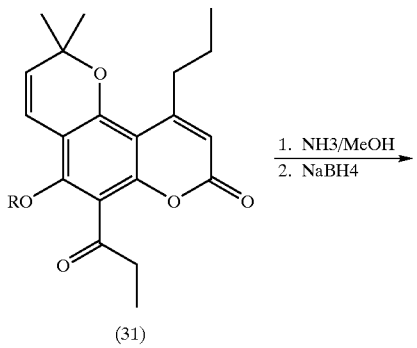

1. NH3/MeOH
2. NaBH4

(31)

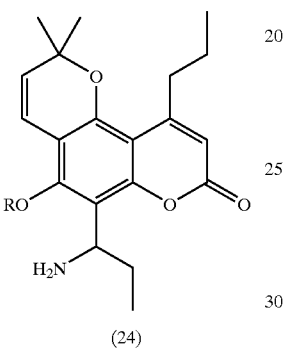

(24)

5-Alkyloxy-2,2-dimethyl-6-propionyl-10-propyl-2H-pyrano[2,3-f]chromen-8-one (31) was dissolved in 7N methanolic ammonia (5–10 mL/mmol). The reaction mixture was stirred at ambient temperature overnight or until the starting material was completely consumed. Volatiles were removed on Rotavapor and the residue was re-dissolved in methanol (5–10 ml/mmol) and the solution was cooled to 0 deg C. Sodium borohydride (5 eq) was added portionwise and the mixture was allowed to reach room temperature. The mixture was stirred for 2 h, quenched with water, diluted with ethyl acetate (50 mL/mmol). The mixture was washed successively with water and brine, dried over anhydrous sodium sulfate and the solution was concentrated on Rotavapor. The desired product was separated on silica gel column eluted with 2–10% methanol in dichloromethane. Compound 24e is the representative and its analytical data is shown below.

6-(1-Aminopropyl)-5-(2-hydroxyethoxy)-2,2-dimethyl-10-propyl-2H-pyrano[2,3-f]chromen-8-one (24e): 47% yield. $^1$H NMR (CDCl$_3$): 0.86 (t, J=7.5 Hz, 3H), 1.03 (t, J=7.5 Hz, 3H), 1.50 (s, 3H), 1.52 (s, 3H), 1.66 (m, 2H), 2.01 (m, 1H), 2.11 (m, 1H), 2.91 (m, 4H), 3.80 (m, 2H), 4.13 (m, 1H), 4.21 (m, 1H), 4.63 (t, J=7.5 Hz, 1H), 5.63 (d, J=10.0 Hz, 1H), 6.02 (s, 1H), 6.50 (J=10.0 Hz, 1H); $^{13}$C NMR (CDCl$_3$): 11.51, 13.97, 23.15, 27.27, 27.58, 29.25, 38.71, 49.23, 61.65, 78.58, 106.36, 110.64, 111.98, 118.02, 127.82, 151.41, 153.77, 158.25, 160.36; IR: 1721 cm$^{-1}$; MS (ACPI+): 388 (M+1), 371 (M+1-NH3); Anal calc for C$_{22}$H$_{29}$O$_5$·1/2H$_2$O: C 66.65, H 7.63, N 3.53. Found C 66.61, H 7.31, N 3.29.

Example 14

N-Substituted 6-(1-aminopropyl)-5-methoxy-2,2-dimethyl-10-propyl-2H-pyrano[2,3-f]chromen-8-one (24)

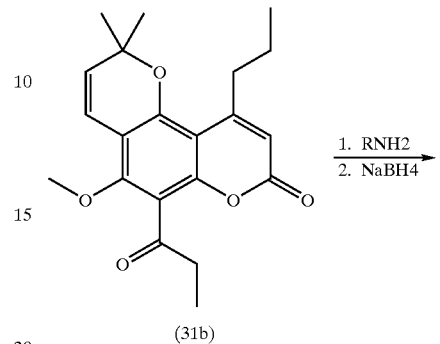

1. RNH2
2. NaBH4

(31b)

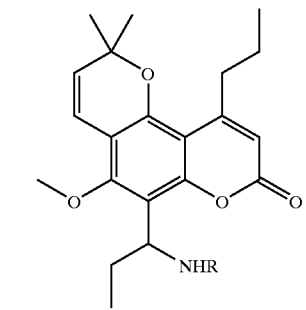

(24)

A solution of 5-methoxy-2,2-dimethyl-6-propionyl-10-propyl-2H-pyrano[2,3-f]chromen-8-one (31b) and an amine (10–40 eq) in methanol or methanol/tetrahydrofurane (50–100 mL per mmol) was stirred until all starting material was consumed (16–36 h). Sodium borohydride (5 eq) was then added portionwise to the reaction mixture and stirring was continued until the reaction was completed (2–4 h). Excess of sodium borohydride was quenched with water and the mixture concentrated under vacuum. The residue was partitioned between water (50 mL/mmol) and ethyl acetate (100 mL/mmol). The organic layer was separated and washed consecutively with water (2×50 mL) and brine. The organic solution was dried over anhydrous sodium sulfate and concentrated. The residue was chromatographed on silica gel column eluted with 2–10% methanol in dichloromethane. Compound 24g is the representative and its analytical data is shown below.

6-(1-Ethylaminopropyl)-5-methoxy-2,2-dimethyl-10-propyl-2H-pyrano[2,3-f]chromen-8-one, hydrochloride (24g): 27% yield. $^1$H NMR (DMSO-d$_6$): 0.85 (t, J=7.0 Hz, 3H), 1.05 (t, J=7.5 Hz, 3H), 1.10 (t, J=7.5 Hz, 3H), 1.50 (s, 3H), 1.52 (s, 3H), 1.66 (m, 2H), 2.09 (m, 1H), 2.52 (m, 4H), 2.91 (m, 2H), 3.80 (s, 3H), 5.64 (d, J=10.0 Hz, 1H), 6.03 (s, 1H), 6.54 (d, J=10.0 Hz, 1H); $^{13}$C NMR (DMSO-d$_6$): 10.76, 13.74, 22.92, 27.23, 37.68, 63.46, 66.31, 77.94, 110.33, 112.33, 116.48, 152.28, 157.23, 157.78, 158.32; IR:1733 cm$^{-1}$; MS (ACPI+): 386 (M+1), 341 (M-C$_2$H$_5$NH$_2$+1); Anal calcd. for C$_{23}$H$_{32}$ClNO$_4$: C 65.47, H 7.64, N 3.32; Found C 65.15, H 7.76, N 3.32.

Example 15

8-(1-Aminopropyl)-5,7-diisopropoxy-4-propyl-chromen-2-one, hydrochloride

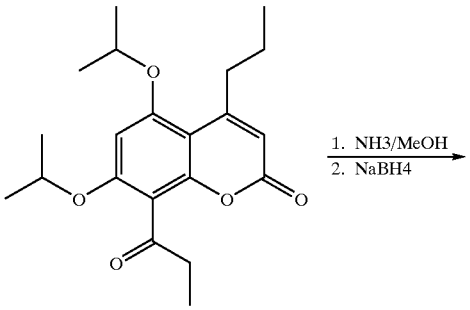

1. NH3/MeOH
2. NaBH4

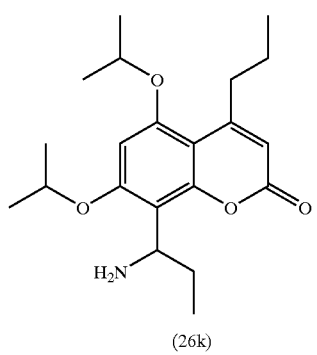

(26k)

The same procedure as used in the preparation of 24e. Compound 26k: 1H NMR (DMSO-d$_6$): 0.77 (t, 3H), 0.98 (t, 3H), 1.36 (d, 12H), 1.57 (m, 2H), 2.05 (m, 2H), 2.87 (m, 2H), 4.62 (bs, 1H), 4.99 (m, 2H), 6.04 (s, 1H), 6.67 (s, 1H), 8.22 (bs, 3H); $^{13}$C NMR (DMSO-d$_6$): 10.39, 13.67, 21.32, 22.94, 38.09, 46.67, 70.65, 71.17, 94.70, 103.05, 104.07, 110.27, 154.32, 156.67, 158.19, 158.78, 158.91; IR: 1720 cm$^{-1}$; MS (APCI+): 362 (M+1), 345 (M-NH$_3$+1); Anal. Calcd. for C$_{21}$H$_{32}$ClNO$_4$.1/2H$_2$O: C 61.98, H 8.17, N 3.44; Found C 61.85, H 8.04, N 3.56.

Example 16

5-Alkyloxy-2,2-dimethyl-6-propionyl-10-propyl-3,4-dihydro-2H-pyrano[2,3-f]chromen-8-one (44)

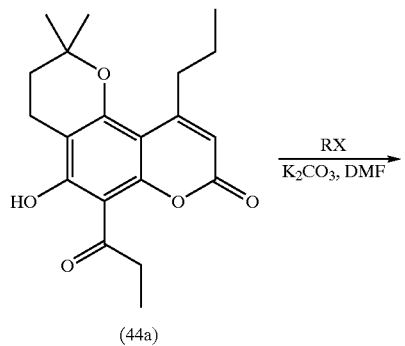

(44a)

RX / K$_2$CO$_3$, DMF →

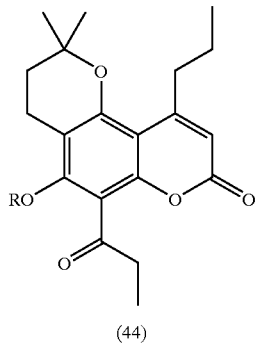

(44)

To a mixture of 5-hydroxy-2,2-dimethyl-6-propionyl-10-propyl-3,4-dihydro-2H-pyrano[2,3-f]chromen-8-one (44a) and potassium carbonate (10 eq) in DMF (15 mL/mmol) was added alkyl halide (2–5 eq) and the reaction was carried out 16 h at ambient temperature. The mixture was partitioned between water (10 volumes of DMF) and ethyl acetate (50 mL/mmol). The organic layer was separated, washed with brine, dried over anhydrous sodium sulfate and concentrated in vacuum. The product was purified by column chromatography. The representative compounds are shown below.

5-Isopropoxy-2,2-dimethyl-6-propionyl-10-propyl-3,4-dihydro-2H-pyrano[2,3-f]chromen-8-one (44i): 89% yield. $^1$H NMR (CDCl$_3$): 1.02 (t, J=7.5 Hz, 3H), 1.24 (d, J=6.0 Hz, 6H), 1.40 (s, 6H), 1.64 (m, 2H), 1.80 (t, J=7,0 Hz, 2H), 2.74 (t, J=6.5 Hz, 2H), 2.90 (m, 4H), 4.26 (m, 1H), 5.99 (s, 1H); $^{13}$C NMR (CDCl$_3$): 7.92, 13.87, 18.20, 22.41, 23.21, 26.68, 31.58, 38.36, 39.02, 76.18, 76.75, 105.87, 111.38, 112.35, 116.90, 151.13, 153.26, 155.54, 157.89, 160.05, 203.53; IR: 1711 cm$^{-1}$; MS (ACPI +): 387 (M+1); Anal. Calcd. for C$_{23}$H$_{30}$O$_5$: C 71.48, H 7.82. Found: C 71.61, H 7.89.

5-(2-Hydroxyethoxy)-2,2-dimethyl-6-propionyl-10-propyl-3,4-dihydro-2H-pyrano[2,3-f]chromen-8-one (44k): 33% yield. $^1$H NMR (CDCl$_3$): 1.03 (t, J=7.5 Hz, 3H), 1.21 (t, J=7.5 Hz, 3H), 1.42 (s, 6H), 1.64 (m, 2H), 1.82 (m, 2H), 2.78 (t, J=6.5 Hz, 2H), 2.91 (m, 4H), 3.05 (t, J=6.5 Hz, 1H), 3.85 (m, 2H), 4.07 (m, 2H), 6.19 (s, 1H); $^{13}$C NMR (CDCl$_3$): 8.05, 13.86, 17.87, 23.18, 26.68, 31.35, 38.59, 39.01, 62.10, 76.47, 76.52, 106.21, 110.46, 112.56, 116.36, 151.49, 153.92, 156.70, 157.93, 159.78, 204.71; IR: 1720, 1694 cm$^{-1}$; MS (ACPI+): 388 (M+1); Anal. Calcd. for C$_{22}$H$_{28}$O$_6$: C 68.02, H 7.27; Found: C 68.03, H 7.30.

2,2-Dimethyl-5-(2-morpholin-4-yl-ethoxy)-6-propionyl-10-propyl-3,4-dihydro-2H-pyrano[2,3-f]-chromen-8-one (44m): 73% yield. $^1$H NMR (CDCl$_3$): 1.02 (t, J=7.5 Hz, 3H), 1.20 (t, J=7.5 Hz, 3H), 1.41 (s, 6H), 1.81 (t, J=7.0 Hz, 2H), 2.53 (m, 4H), 2.70 (t, J=5.0 Hz, 2H), 2.78 (t, J=7.0 Hz, 2H), 2.91 (m, 4H), 3.73 (t, J=4.5 Hz, 4H), 4.00 (t, J=5.0 Hz, 2H), 6.01 (s, 1H); $^{13}$C NMR (CDCl$_3$): 7.92, 13.85, 17.34, 23.18, 26.67, 31.37, 38.45, 38.97, 53.87, 58.32, 66.85, 71.76, 76.33, 106.33, 110.86, 112.59, 116.97, 151.15, 153.45, 156.40, 157.87, 159.87, 203.50; IR: 1713 cm$^{-1}$; MS (ACPI+): 458 (M+1); Anal. Calcd. for C$_{26}$H$_{35}$NO$_6$: C 68.25, H 7.71, N 3.06. Found: C 68.13, H 7.76, N 3.04.

5-Ethoxycarbonylmethyl-2,2-dimethyl-6-propionyl-10-propyl-3,4-dihydro-2H,8H-pyrano[2,3-f]chromen-8-one (44n): 81% yield. $^1$H NMR (CDCl$_3$): 1.03 (t, J=7.5 Hz, 3H), 1.21 (t, J=7.5 Hz, 3H), 1.41 (s, 6H), 1.63 (m, 2H), 1.84 (t, J=6.5 Hz, 2H), 2.70 (t, J=7.0 Hz, 2H), 2.91 (m, 4H), 4.09 (t, J=4.5 Hz, 2H), 4.34 (t, J=4.5 Hz, 2H), 6.02 (s, 1H); $^{13}$C NMR (CDCl$_3$): 7.92, 13.83, 17.20, 20.79, 23.16, 26.64, 31.30, 38.46, 38.95, 63.13, 72.46, 77.39, 106.48, 110.77, 112.71, 116.87, 151.20, 153.51, 155.78, 157.79, 159.75, 170.74, 203.26; IR: 1727 cm$^{-1}$; MS (ACPI+): 331 (M+1); Anal. Calcd. for C$_{24}$H$_{30}$O$_7$: C 66.96, H 7.02; Found: C 69.76, H 7.02.

Example 17

5-Hydroxy-2,2-dimethyl-6-propionyl-10-propyl-3,4-dihydro-2H-pyrano[2,3-f]chromen-8-one (44a)

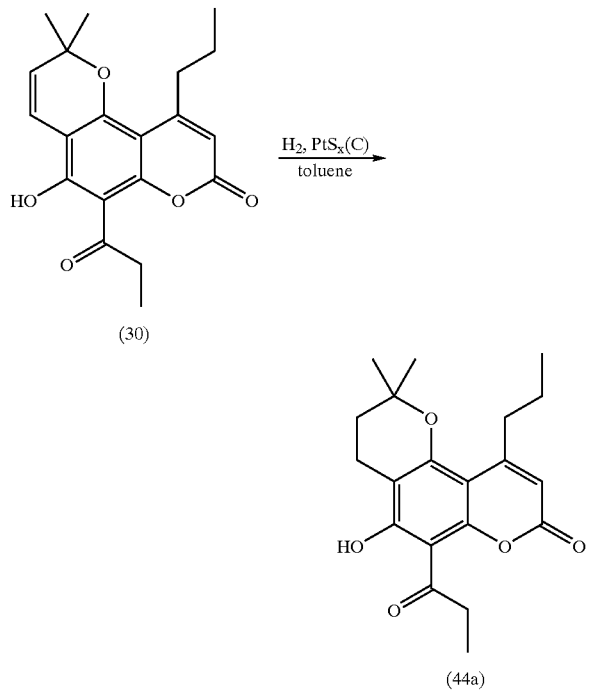

A mixture of 5-hydroxy-2,2-dimethyl-6-propionyl-10-propyl-2H-pyrano[2,3-f]chromen-8-one (30) (5 g, 14.60 mmol) and sulfided platinum (5% on carbon, 1 g) in toluene/isopropyl alcohol (200/50 mL) was hydrogenated 16 h at room temperature under atmospheric pressure of hydrogen. The catalyst was filtered off and the filtrate concentrated under vacuum. The solid residue was crystallized from ethanol and re-crystallized from acetone to provide 2.66 g of 44a (53% yield). $^1$H NMR (CDCl$_3$): 1.03 (t, J=7.5 Hz, 3H), 1.23 (t, J=7.5 Hz, 3H), 1.42 (s, 6H), 1.64 (m, 2H), 1.84 (t, J=6.5 Hz, 2H), 2.70 (t, J=6.5 Hz, 2H), 2.90 (m, 2H), 3.34 (q, J=7.0 Hz, 2H), 5.98 (s, 1H), 14.61 (s, 1H); $^{13}$C NMR (CDCl$_3$): 8.45, 13.89, 16.42, 23.37, 26.62, 31.20, 38.13, 39.38, 77.60, 102.77, 103.43, 105.30, 110.22, 156.41, 157.29, 158.94, 159.76, 165.77, 206.67; IR: 1730 cm$^{-1}$; MS (ACPI+): 345 (M+1); Anal. Calcd. for C$_{20}$H$_{24}$O$_5$: C 69.75, H 7.02; Found C 70.03, H 7.18.

Example 18

5-Alkyloxy-2,2-dimethyl-6-propionyl-10-propyl-3,4-dihydro-2H-pyrano[2,3-f]chromen-8-one (44)

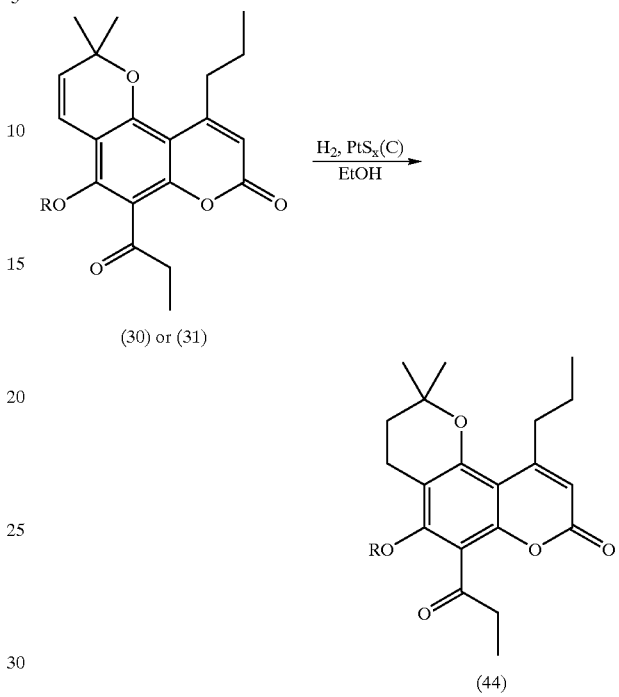

A solution of 5-alkyloxy-2,2-dimethyl-6-propionyl-10-propyl-2H-pyrano[2,3-f]chromen-8-one (30 or 31) in ethanol (30–100 mL/mmol) was hydrogenated under atmospheric pressure of hydrogen in the presence of sulfided platinum (Aldrich, 5% on carbon, 100 mg/mmol). The reaction was carried out overnight at ambient temperature. The mixture was filtered through a pad of Celite and the filtrate concentrated under vacuum. The residue was chromatographed on silica gel column eluted with 15–30% ethyl acetate in hexanes. Compound 44b is the representative and its analytical data is shown below.

5-Methoxy-2,2-dimethyl-6-propionyl-10-propyl-3,4-dihydro-2H-pyrano[2,3-f]chromen-8-one (44b): 68% yield. $^1$H NMR (CDCl$_3$): 1.02 (t, J=7.5 Hz, 3H), 1.22 (t, J=7.5 Hz, 3H), 1.41 (s, 6H), 1.62 (m, 2H), 1.82 (t, J=6.5 Hz, 2H), 2.75 (t, J=6.5 Hz, 2H), 2.91 (m, 4H), 3.78 (s, 3H), 6.01 (s, 1H); $^{13}$C NMR (CDCl$_3$): 7.97, 13.84, 17.20, 23.19, 26.66, 31.33, 38.48, 38.99, 62.14, 76.35, 106.14, 110.66, 112.48, 116.55, 151.24, 153.50, 157.51, 157.92, 159.92, 203.40; IR: 1724, 1704 cm$^{-1}$; MS (ACPI+): 359 (M+1); Anal. Calcd. for C$_{21}$H$_{26}$O$_5$: C 70.37, H 7.31; Found: C 70.15, H 7.28.

Example 20

Evaluation of Compounds Synthesized for Activity against *M. tuberculosis*

The compounds synthesized above were evaluated for activity against *M. tuberculosis* H37Ra using a colorimetric microdilution broth assay that incorporated the REDOX indicator alamar Blue, which indicates the growth and viability by the metabolic reduction of the dye from blue to red[18].

In an initial screen, the compounds were assayed in duplicate at four log$_{10}$ dilutions, with the highest concentration being 128 μg/mL (therefore, tested concentrations were 0.128, 1.28, 12.8, and 128 μg/mL). Each solubilized test compound was diluted in broth medium (Middlebrook 7H9+ADC enrichment+0.2% glycerol) at twice the desired concentration and 0.05 mL of each dilution then added to appropriate wells in duplicate in a 96 well (U-shaped) microtiter plates. A plate format was designed for up to seven (7) compounds per plate. Each plate also included uninoculated drug controls, viability controls, uninoculated medium controls, and positive drug controls. The inoculum for each well consisted of 0.05 mL of culture, standardized as described above to provide an inoculum in each microtiter well of approximately $10^5$ CFU/mL. The plates were covered with a lid, placed in polyethylene bags and incubated for at 37° C. for 6 days. At that time, alamar Blue, diluted in Tween 80, was added to each well followed by further incubation for about 20 hours. The plates were read in an optical microplate reader programmed to subtract absorbance at 600 nm from absorbance at 570 nm. This effectively blanked out turbidity and absorbance due to oxidized dye. The amount of dye reduced, resulting in a change from blue to red, is indicative of drug yielding a differential absorption of zero or less. The initial screening results are shown in Table 3.

The method is easily modified to medium or high throughput screening in order to evaluate more compounds. For example, instead of 4 concentrations in duplicate, the compounds are tested singly at one cut-off concentration (e.g., 12.8 μg/mL).

TABLE 3

Activity of Compounds against M. tuberculosis H37Ra from the Initial Screening

| Type I Compounds | | | | Type II Compounds | | |
|---|---|---|---|---|---|---|
| 11 | | 12 | | trans-17 | | cis-17 |
| $R_1$ | MIC | $R_1$ | MIC | $R_1$ | MIC of trans-17 | MIC of cis-17 |
| a. H | >12.8<128 | a. H | >12.8<128 | a. H | | |
| b. Me (9) | >12.8<128 | b. Me | >12.8<128 | b. Me | >12.8<128 | >128 |
| c. Et | >12.8<128 | c. Et | >128 | e. i-Pr | >12.8<128 | >1.28<12.8 |
| d. CH≡CCH$_2$ | >12.8<128 | d. CH≡CCH$_2$ | >12.8<128 | d. CH≡CCH$_2$ | >128 | >12.8<128 |
| e. HOCH$_2$CH$_2$ | >12.8<128 | e. HOCH$_2$CH$_2$ | >12.8<128 | c. CH$_2$=CHCH$_2$ | >128 | >12.8<128 |
| | | | | f, CH$_2$=CHCH(CH$_3$) | >12.8<128 | >1.28<12.8 |
| | | | | g, CH$_2$=C(CH$_3$)CH$_2$ | >128 | >12.8<128 |

| Type III | | Type IV Compounds | | | | |
|---|---|---|---|---|---|---|
| 21 | | 31 | | 29 | | 22 |
| $R_1$ | MIC | $R_1$ | MIC | $R_1$ | MIC | MIC |
| a, H | N/P | 30.H | >128 | a,H | >12.8<128 | >1.28 <12.8 |
| b, Me | >12.8 <128 | 31b. Me | >12.8<128 | b, Me | >128 | |
| c, i-Pr | >128 | 31c.Et | >128 | c, i-Pr | >128 | |
| d, CH$_2$=CHCH$_2$ | >1.28<12.8 | 31d. CH≡CCH$_2$ | >128 | d, CH$_2$=CHCH$_2$ | >128 | |
| | | 31e. HOCH$_2$CH$_2$ | >12.8<128 | | | |
| | | 31f. Ac | >12.8<128 | | | |

| Type IV Compounds | Others |
|---|---|

TABLE 3-continued

Activity of Compounds against M. tuberculosis H37Ra from the Initial Screening

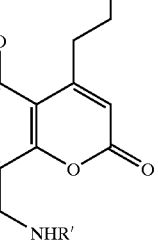

| R₁/R' | MIC | R₁ | MIC | R₁ | MIC | Cmpd | MIC |
|---|---|---|---|---|---|---|---|
| a, H/H | >12.8<128 | a,H | N/P | a.H | >128 | 47 | >12.8<128 |
| b, Me/H | >12.8<128 | b, Me | >12.8<128 | b. Me | >1.28<12.8 | 48 | >12.8<128 |
| c, Et/H | | c, i-Pr | >1.28<12.8 | c.Et | >128 | | |
| d, CH=CCH₂/H | | d, CH=CHCH₂ | >12.8<128 | d. CH=CCH₂ | >128 | | |
| e, HOCH₂CH₂/H | >1.28<12.8 | | | e. HOCH₂CH₂ | >12.8<128 | | |
| f, Me/Me | | | | f. AcOCH₂CH₂ | >12.8<128 | | |
| g, Me/Et | >12.8<128 | | | g, CH₂CHCH₂ | >128 | | |
| h, Me/i-Pr | | | | h, i-Pr | >128 | | |
| i, Me/HOCH₂CH₂ | | | >12.8<128 | i, EtO₂CCH₂ | >128 | | |
| j, Me/Bn | | | | j, Ac | >128 | | |
| k, i-Pr/H | | | | k,Ts | >128 | | |
| l, Allyl/H | | | | l, $\begin{array}{c}\text{O}\\ \diagup\diagdown\\ \text{N—CH}_2\text{CH}_2\end{array}$ | >128 | | |
| | | | | m. MeOCH₂ | >128 | | |

MIC: μg/mL

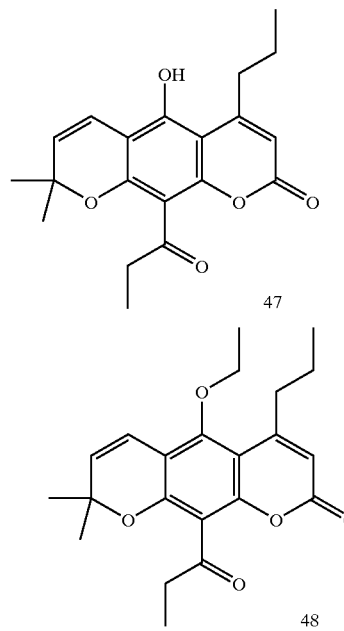

47

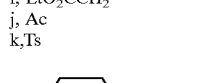

48

Compounds exhibiting activity, with MIC range less than 12.8 μg/mL, in the initial screening were further assayed again within an appropriate concentration range using 2-fold dilutions to determine the minimum inhibitory concentration (MIC), which is defined as the lowest concentration of drug that completely inhibits growth of M. tuberculosis, as well as the MBC (minimum bactericidal concentration). The results are shown in Table 4. Four of the compounds (cis-17c, 22, 45e, and 26c) were bactericidal in their effect on M. tuberculosis since their MIC/MBC were 4 or less. All of these compounds had an MIC value of 16 μg/mL.

TABLE 4

MIC and MBC Values of Compounds against *M. tuberculosis* H37Ra

| Compound | MIC | MBC | MIC/MBC |
|---|---|---|---|
| cis-17c | 16 | 64 | 4 |
| cis-17f | 16 | >64 | >4 |
| 21d | 16 | >64 | >4 |
| 22 | 16 | 32 | 2 |
| 45e | 16 | 32 | 2 |
| 26c | 16 | 64 | 4 |
| 44b | 16 | >64 | >4 |

MIC and MBC: μg/mL

LITERATURE REFERENCES

1. Lopez, A. in *Disease Control Priorties in Developing Countries,* Jamison, D. T., Mosely, W. H. Eds. (Oxford Univ. Press for the World Bank, New York, 1992), p.21.
2. Murray, C. J. L.; Styblo, K.; Rouillon, A. in *Disease Control Priorties in Developing Countries,* Jamison, D. T., Mosely, W. H. Eds. (Oxford Univ. Press for the World Bank, New York, 1992), p.50; *Bull. Int. Union Tuberc.* 1990; 65: 24.
3. Stokstad, E. *Scinece,* 2000; 287: 2391.
4. Raviglione, M. C.; Snider, D. E.; Koch, A. *JAMA,* 1995; 273: 220.
5. Harries, A. D.; Mahler, D. TB/HIV A Clinical Manual Published by the World Health Organization 1996, Printer: Stabilimento Tipografico Ferrero s.r.l.-Romano Canavese [TO], Italy.
6. Barrow, E. L. W.; Winchester, G. A.; Stass, J. K.; Quenelle, D. C.; Barrow, W. W. *Antimicrob. Agents Chemother.* 1998; 42: 2682–2689.
7. Kling, J. *Modern Drug Discovery,* 1999; (Jan/Feb): 32–45.
8. Heifets, L.; Sanchez, T.; Vanderkolk, J.; Pham, V. *Antimicrob. Agents Chemother.* 1999; 43: 25–28.
9. Xu, Z.-Q.; Jenta, T. R.; Flavin, M. T. *Current Opinion for Drug Discovery & Development,* 2000; 3: 155–166.
10. Zembower, D. E.; Liao, S.; Flavin, M. T.; Xu, Z.-Q.; Stup, T. L.; Buckheit, R. W., Jr.; Khilevich, A.; Mar, A. A.; Sheinkman; A. K. *J. Med. Chem.* 1997; 40: 1005.
11. Galinis, D. L.; Fuller, R. W.; McKee, T. C.; Cardellina, J. H., II; Gulakowski, R. J.; McMahon, J. B.; Boyd, M. R. *J. Med. Chem.* 1996; 39: 4507.
12. Deshapande, P. P.; Tagliaferri. F.; Victory. S. F.; Yan, S.; Baker, D. C. *J. Org. Chem.* 1995; 60: 2964–2965.
13. Zembower, D. E.; Chandrasekar, P.; Liao, S.; Xu, Z.-Q.; Flavin, M. T. 213*th National Meeting of the American Chemical Society, Division of Medicinal Chemistry,* San Francisco, Apr. 13–17, 1997, Abstract 111.
14. Flavin, M. T.; Rizzo, J. D.; Khilevich, A.; Kucherenko, A.; Sheinkman, A. K.; Vilaychack, V.; Lin, L.; Chen, W.; Mata, E.; Pengsuparp, T.; Pezzuto, J. M.; Hughes, S. H.; Flavin, T. M.; Cibulski, M.; Boulanger, W. A.; Shone, R. L.; Xu, Z.-Q. *J. Med. Chem.* 1996; 39: 1303–1313.
15. Kucherenko, A.; Flavin, M. T.; Boulanger, W. A.; Khilevich, A.; Shone, R. L.; Rizzo, J. D.; Sheinkman, A. K.; Xu, Z.-Q. *Tetrahedron Lett.* 1995; 36: 5475–5478.
16. Lane, C. F. *Synthesis,* 1975: 135–146.
17. Fabiano, E.; Golding, B. T.; Sadeghi, M. M. *Synthesis,* 1987: 190–192.
18. Suling, W. J.; Reynolds, R. C.; Barrow, E. W.; Wilson, L. N.; Piper, J. R.; Barrow, W. W., *Antimicrob. Agents Chemother.,* 1998; 42: 811.
19. Duncan, K. *J. Pharm. Pharmacol.* 1997; 49 (Suppl. 1): 21.

We claim:

1. A compound according to formula (I) or a pharmaceutically acceptable salt thereof:

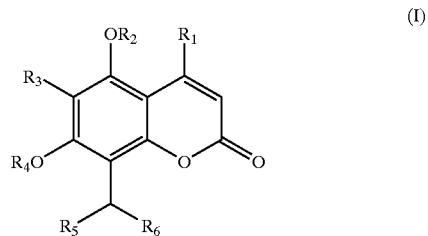

(I)

wherein $R_1$ is alkyl, alkenyl, alkynyl, aryl, OH, or $NH_2$;

$R_2$ is selected from H, alkyl, alkenyl, alkynyl, aryl, and can optionally form a 4 to 7-membered ring with $R_3$;

$R_3$ is selected from H, alkyl, alkenyl, alkynyl, aryl, and can optionally form a 4 to 7-membered ring with $R_2$;

$R_4$ is selected from H, alkyl, alkenyl, alkynyl, aryl, and can optionally form a 4 to 7-membered ring with $R_5$;

$R_5$ is selected from H, alkyl, alkenyl, alkynyl, aryl, and can optionally form a 4 to 7-membered ring with $R_4$; and $R_6$ is selected from the group consisting of =O, OH, =NH, $NH_2$, SH, $P(O)_nH_m$ substituted imines, and substituted amines, wherein n is 2–4 and m is 1–3;

with the proviso that only one of either $R_2$ and $R_3$ or $R_4$ and $R_5$ optionally form a 6-membered ring, resulting in a compound of formula (I) comprising three fused 6-membered rings.

2. The compound of claim 1, wherein the optionally formed 4 to 7-membered ring between $R_2$ and $R_3$ is a 6-membered ring.

3. The compound of claim 1, wherein the optionally formed 4 to 7-membered ring between $R_4$ and $R_5$ is a 6-membered ring.

4. The compound of claim 1, wherein the compound is:

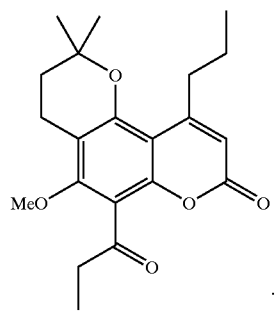

5. The compound of claim 1, wherein the compound is:

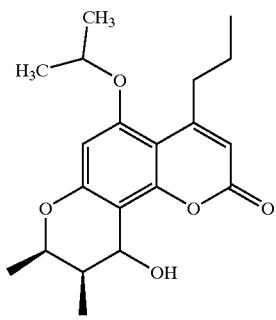

6. The compound of claim 1, wherein the compound is:

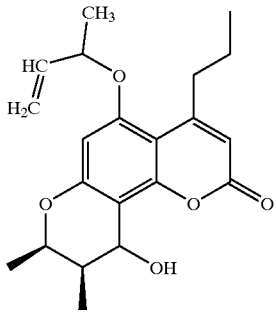

7. The compound of claim 1, wherein the compound is:

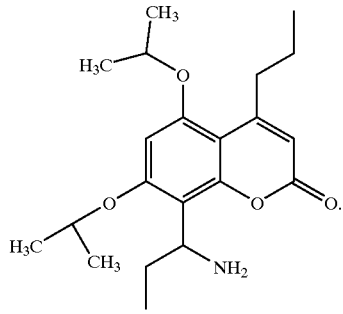

8. The compound of claim 1, wherein the compound is:

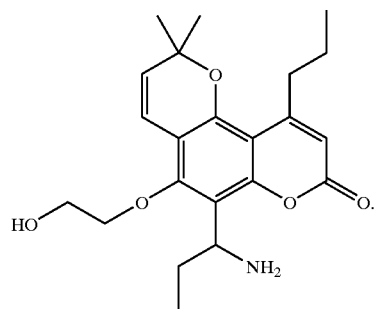

9. The compound of claim 1, wherein the compound is:

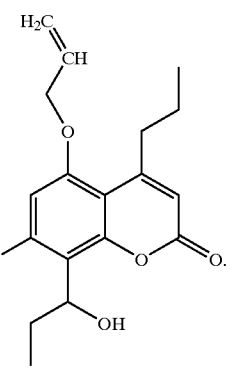

10. A compound of the formula:

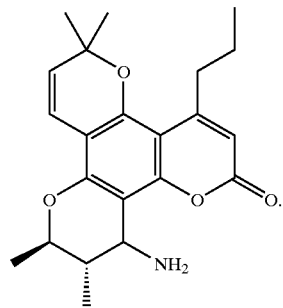

11. A composition comprising a compound according to formula I, and a pharmaceutically acceptable carrier:

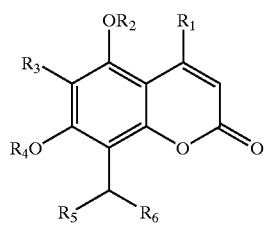

(I)

wherein $R_1$ is alkyl, alkenyl, alkynyl, aryl, OH, or $NH_2$;

$R_2$ is selected from H, alkyl, alkenyl, alkynyl, aryl, and can optionally form a 4 to 7-membered ring with $R_3$;

R₃ is selected from H, alkyl, alkenyl, alkynyl, aryl, and can optionally form a 4 to 7-membered ring with R₂;

R₄ is selected from H, alkyl, alkenyl, alkynyl, aryl, and can optionally form a 4 to 7-membered ring with R₅;

R₅ is selected from H, alkyl, alkenyl, alkynyl, aryl, and can optionally form a 4 to 7-membered ring with R₄; and R₆ is selected from the group consisting of =O, OH, =NH, NH₂, SH, $P(O)_nH_m$ substituted imines, and substituted amines, wherein n is 2–4 and m is 1–3;

with the proviso that only one of either R₂ and R₃ or R₄ and R₅ optionally form a 6-membered ring, resulting in a compound of formula (I) comprising three fused 6-membered rings.

12. The composition of claim 11, wherein the optionally formed 4 to 7-membered ring between R₂ and R₃ is a 6-membered ring.

13. The composition of claim 11, wherein the optionally formed 4 to 7-membered ring between R₄ and R₅ is a 6-membered ring.

14. A composition comprising the compound

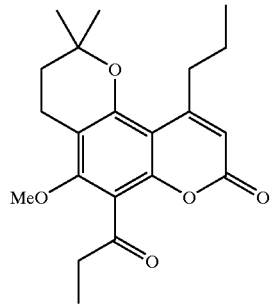

and a pharmaceutically acceptable carrier.

15. A composition comprising the compound

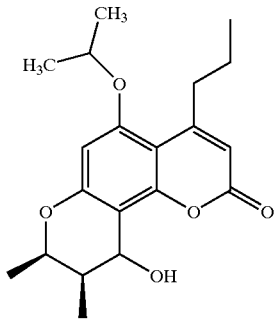

and a pharmaceutically acceptable carrier.

16. A composition comprising the compound

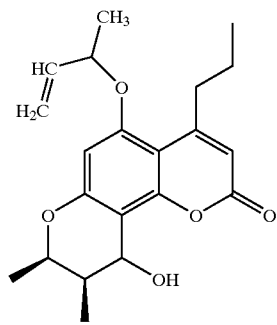

and a pharmaceutically acceptable carrier.

17. A composition comprising the compound

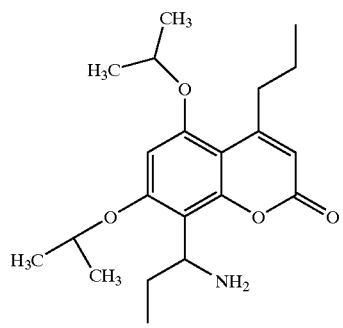

and a pharmaceutically acceptable carrier.

18. A composition comprising the compound

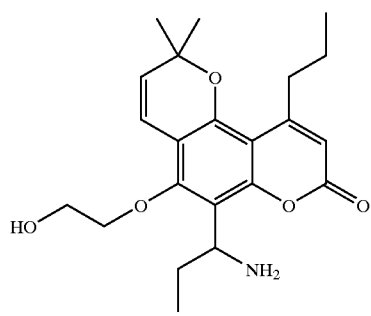

and a pharmaceutically acceptable carrier.

19. A composition comprising the compound

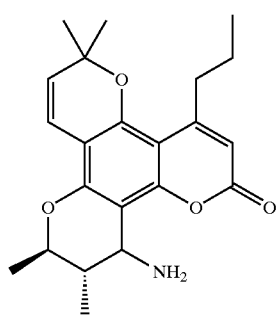

and a pharmaceutically acceptable carrier.

20. A composition comprising the compound

[chemical structure: coumarin with allyloxy groups and propyl, CH(OH)ethyl substituents]

and a pharmaceutically acceptable carrier.

21. A method of treating infection or conditions related to infection by Mycobacterium in a mammal in need of such treatment comprising administering a therapeutically effective amount of a composition comprising one or more non-toxic pharmaceutically acceptable carriers and a compound of Formula (I) or a pharmaceutically acceptable salt thereof:

[chemical structure of Formula (I): coumarin with OR₂, R₁, R₃, R₄O, and CH(R₅)(R₆) substituents]
(I)

wherein $R_1$ is alkyl, alkenyl, alkynyl, aryl, OH, or $NH_2$;

$R_2$ is selected from H, alkyl, alkenyl, alkynyl, aryl, and can optionally form a 4 to 7-membered ring with $R_3$;

$R_3$ is selected from H, alkyl, alkenyl, alkynyl, aryl, and can optionally form a 4 to 7-membered ring with $R_2$;

$R_4$ is selected from H, alkyl, alkenyl, alkynyl, aryl, and can optionally form a 4 to 7-membered ring with $R_5$;

$R_5$ is selected from H, alkyl, alkenyl, alkynyl, aryl, and can optionally form a 4 to 7-membered ring with $R_4$; and $R_6$ is selected from the group consisting of =O, OH, =NH, $NH_2$, SH, $P(O)_nH_m$ substituted imines, and substituted amines, wherein n is 2–4 and m is 1–3;

with the proviso that only one of either $R_2$ and $R_3$ or $R_4$ and $R_5$ optionally form a 6-membered ring, resulting in a compound of formula (I) comprising three fused 6-membered rings.

22. The method of claim 21, wherein the compound of formula (I) is selected from the group consisting of:

[several chemical structures of coumarin derivatives]

; and

[additional chemical structure]

.

23. The method of claim 21, wherein the Mycobacterium is selected from the group consisting of *Mycobacterium avium* complex (MAC), *Mycobacterium kansaii, Mycobac-* terium marinum, Mycobacterium phlei, Mycobacterium ulcerans, Mycobacterium xenopi, Mycobacterium gordonae, Mycobacterium terrae complex, Mycobacterium haemophilum, Mycobacterium fortuitum, Mycobacterium tuberculosis, Mycobacterium laprae, Mycobacterium scrofulaceum and Mycobacterium smegmatis.

24. The method of claim 21, wherein the Mycobacterium is Mycobacterium tuberculosis.

25. A method of treating infection or conditions related to infection by Mycobacterium in a mammal in need of such treatment wherein the Mycobacterium is selected from the group consisting of Mycobacterium avium complex (MAC), Mycobacterium kansaii, Mycobacterium marinum, Mycobacterium phlei, Mycobacterium ulcerans, Mycobacterium xenopi, Mycobacterium gordonae, Mycobacterium terrae complex, Mycobacterium haemophilum, Mycobacterium fortuitum, Mycobacterium tuberculosis, Mycobacterium laprae, Mycobacterium scrofulaceum and Mycobacterium smegmatis, comprising administering to the mammal a compound according to any of claims 2–10, or a pharmaceutically acceptable salt thereof.

26. A method of treating infection or conditions related to infection by Mycobacterium in a mammal in need of such treatment wherein the Mycobacterium is Mycobacterium tuberculosis, comprising administering to the mammal a compound according to any of claims 2–10, or a pharmaceutically acceptable salt thereof.

27. A method of treating a patient who has a disease or condition selected from the group consisting of tuberculosis, tuberculosis associated with immunosuppression, tuberculosis associated with an immunodeficiency, tuberculosis associated with infection by human immunodeficiency virus (HIV), and tuberculosis associated with acquired immune deficiency syndrome (AIDS) and who is in need of such treatment which includes administration of a therapeutically effective amount of a compound of formula (I), or a pharmaceutically acceptable salt thereof:

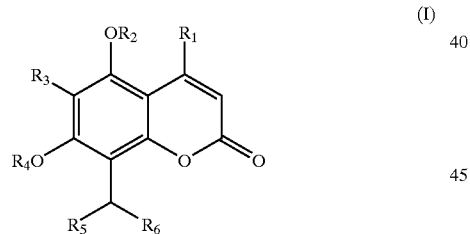

(I)

wherein
$R_1$ is alkyl, alkenyl, alkynyl, aryl, OH, or $NH_2$;
$R_2$ is selected from H, alkyl, alkenyl, alkynyl, aryl, and can optionally form a 4 to 7-membered ring with $R_3$;
$R_3$ is selected from H, alkyl, alkenyl, alkynyl, aryl, and can optionally form a 4 to 7-membered ring with $R_2$;
$R_4$ is selected from H, alkyl, alkenyl, alkynyl, aryl, and can optionally form a 4 to 7-membered ring with $R_5$;
$R_5$ is selected from H, alkyl, alkenyl, alkynyl, aryl, and can optionally form a 4 to 7-membered ring with $R_4$; and
$R_6$ is selected from the group consisting of =O, OH, =NH, $NH_2$, SH, $P(O)_nH_m$ substituted imines, and substituted amines, wherein n is 2–4 and m is 1–3;
with the proviso that only one of either $R_2$ and $R_3$ or $R_4$ and $R_5$ optionally form a 6-membered ring, resulting in a compound of formula (I) comprising three fused 6-membered rings.

28. The method of claim 27, wherein the compound of formula (I) is selected from the group consisting of:

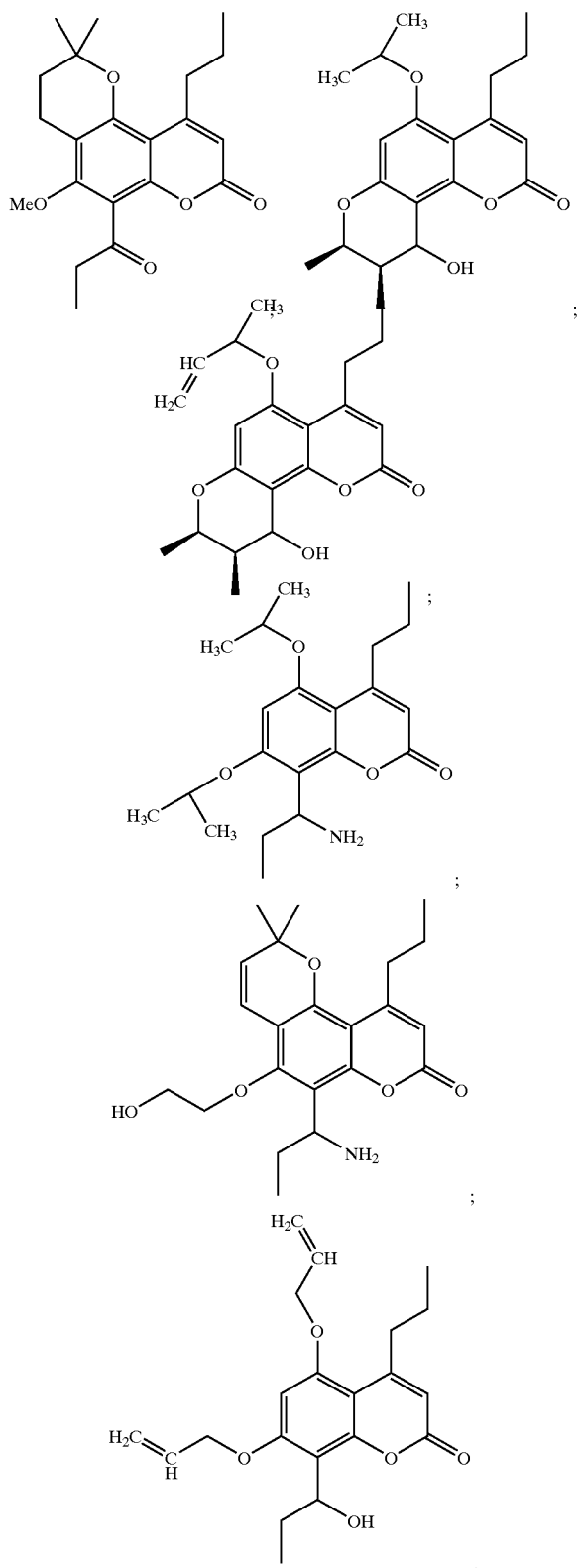

29. A compound according to formula (I) or a pharmaceutically acceptable salt thereof:

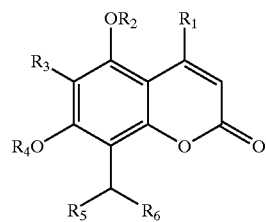

wherein
- $R_1$ is alkyl, alkenyl, alkynyl, aryl, OH, or $NH_2$;
- $R_2$ is selected from H, alkyl, alkenyl, alkynyl, aryl, and can optionally form a 4 to 7-membered ring with $R_3$;
- $R_3$ is selected from H, alkyl, alkenyl, alkynyl, aryl, and can optionally form a 4 to 7-membered ring with $R_2$;
- $R_4$ is selected from H, alkyl, alkenyl, alkynyl, aryl, and can optionally form a 4 to 7-membered ring with $R_5$;
- $R_5$ is selected from H, alkyl, alkenyl, alkynyl, aryl, and can optionally form a 4 to 7-membered ring with $R_4$; and
- $R_6$ is selected from the group consisting of =O, OH, =NH, $NH_2$, SH, $P(O)_n H_m$ substituted imines, and substituted amines, wherein n is 2–4 and m is 1–3;

with the proviso that if both $R_2$ and $R_3$, and $R_4$ and $R_5$ form a six-membered ring, then $R_6$ cannot be =O or OH.

30. A composition comprising the compound of claim 29 and a pharmaceutically acceptable carrier.

31. A method of treating infection or conditions related to infection by Mycobacterium in a mammal in need of such treatment comprising administering a therapeutically effective amount a compound of claim 29 or a pharmaceutically acceptable salt thereof.

32. A method of treating infection or conditions related to infection by Mycobacterium in a mammal in need of such treatment comprising administering a therapeutically effective amount of a composition comprising one or more non-toxic pharmaceutically acceptable carriers and a compound of claim 29 or a pharmaceutically acceptable salt thereof.

33. A method of treating infection or conditions related to infection by Mycobacterium in a mammal in need of such treatment comprising administering a therapeutically effective amount of the compound of claim 10 or a pharmaceutically acceptable salt thereof.

34. A method of treating infection or conditions related to infection by Mycobacterium in a mammal in need of such treatment comprising administering a therapeutically effective amount of a composition comprising one or more non-toxic pharmaceutically acceptable carriers and the compound of claim 10 or a pharmaceutically acceptable salt thereof.

35. A method of treating a patient who has a disease or condition selected from the group consisting of tuberculosis, tuberculosis associated with immunosuppression, tuberculosis associated with an immunodeficiency, tuberculosis associated with infection by human immunodeficiency virus (HIV), and tuberculosis associated with acquired immune deficiency syndrome (AIDS) and who is in need of such treatment which includes administration of a therapeutically effective amount of a compound of claim 10 or a pharmaceutically acceptable salt thereof.

* * * * *